United States Patent
Reicher et al.

(10) Patent No.: US 10,276,265 B2
(45) Date of Patent: Apr. 30, 2019

(54) AUTOMATED ANATOMICALLY-BASED REPORTING OF MEDICAL IMAGES VIA IMAGE ANNOTATION

(71) Applicant: International Business Machines Corporation, Armonk, NY (US)

(72) Inventors: Murray A. Reicher, Rancho Santa Fe, CA (US); Flora Gilboa-Solomon, Haifa (IL); Guy Amit, Ganei Tikva (IL)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/253,746

(22) Filed: Aug. 31, 2016

(65) Prior Publication Data

US 2018/0060533 A1    Mar. 1, 2018

(51) Int. Cl.
   *G06K 9/00*    (2006.01)
   *G16H 15/00*    (2018.01)
   *G06F 19/00*    (2018.01)

(52) U.S. Cl.
   CPC ............. *G16H 15/00* (2018.01); *G06F 19/00* (2013.01); *G06F 19/321* (2013.01)

(58) Field of Classification Search
   CPC ..................... G06F 19/3487; G06F 19/321
   USPC ....................................................... 382/128
   See application file for complete search history.

(56) References Cited

U.S. PATENT DOCUMENTS

| | | | |
|---|---|---|---|
| 3,951,062 A | 4/1976 | Abramson | |
| D394,853 S | 6/1998 | Levin et al. | |
| D403,673 S | 1/1999 | Arora et al. | |
| 7,085,726 B1 | 8/2006 | Galperin et al. | |
| 7,113,946 B2 | 9/2006 | Cosic | |
| D602,942 S | 10/2009 | Bennett et al. | |
| D603,421 S | 11/2009 | Ebeling et al. | |
| 7,783,094 B2 | 8/2010 | Collins et al. | |
| 7,793,217 B1 | 9/2010 | Kim et al. | |
| 8,014,576 B2 | 9/2011 | Collins et al. | |

(Continued)

FOREIGN PATENT DOCUMENTS

| | | |
|---|---|---|
| CN | 101076724 A | 11/2007 |
| CN | 101203747 A | 6/2008 |

(Continued)

OTHER PUBLICATIONS

International Search Report and Written Opinion for Application No. PCT/IB2017/054601 dated Nov. 22, 2017 (10 pages).

(Continued)

*Primary Examiner* — Van D Huynh
(74) *Attorney, Agent, or Firm* — Michael Best & Friedrich LLP

(57) ABSTRACT

Methods and systems for generating an electronic structured report associated with a displayed electronic medical image. One method includes receiving an annotation for the electronic medical image, automatically determining, with an electronic processor, an anatomical location within the electronic medical image associated with the annotation, and automatically determining, with the electronic processor, a location within the electronic structured report associated with the anatomical location based on a predetermined mapping. The method also includes automatically populating the location of the electronic structured report based on the annotation.

18 Claims, 21 Drawing Sheets

(56) References Cited

U.S. PATENT DOCUMENTS

| | | | |
|---|---|---|---|
| 8,015,046 | B2 | 9/2011 | Hagmann et al. |
| D649,557 | S | 11/2011 | Duchene |
| D667,842 | S | 9/2012 | Ouilhet |
| D668,673 | S | 10/2012 | Molino et al. |
| D683,757 | S | 6/2013 | Phelan |
| D684,184 | S | 6/2013 | Tanghe et al. |
| 8,805,879 | B2 | 8/2014 | Kelley et al. |
| 8,839,135 | B2 | 9/2014 | Vander Griend et al. |
| D715,834 | S | 10/2014 | Siddons |
| D719,186 | S | 12/2014 | Kim |
| D724,621 | S | 3/2015 | Rydenhag et al. |
| 9,014,485 | B2 | 4/2015 | Moehrle |
| 9,158,441 | B2 | 10/2015 | Hilton et al. |
| D744,529 | S | 12/2015 | Guzman et al. |
| D744,531 | S | 12/2015 | Jung |
| 9,250,869 | B1 | 2/2016 | Tsai et al. |
| D763,312 | S | 8/2016 | Vaysman |
| D764,497 | S | 8/2016 | Seo et al. |
| 9,418,082 | B2 | 8/2016 | Mukhin et al. |
| D766,948 | S | 9/2016 | Gebauer et al. |
| 9,460,304 | B1 | 10/2016 | Tsai et al. |
| D774,085 | S | 12/2016 | Montes et al. |
| D775,174 | S | 12/2016 | Chen et al. |
| D776,680 | S | 1/2017 | Bae et al. |
| D781,906 | S | 3/2017 | Yu |
| D781,911 | S | 3/2017 | Tegethoff |
| D782,535 | S | 3/2017 | Menz et al. |
| 9,588,944 | B2 | 3/2017 | Ferraro et al. |
| D788,161 | S | 5/2017 | Bauer et al. |
| D789,416 | S | 6/2017 | Baluja et al. |
| D790,593 | S | 6/2017 | Zhong et al. |
| D795,294 | S | 8/2017 | Faulkner et al. |
| D802,014 | S | 11/2017 | Dragoi et al. |
| D802,016 | S | 11/2017 | Kwiatkowski et al. |
| D805,104 | S | 12/2017 | Hashimoto et al. |
| D806,116 | S | 12/2017 | Springer |
| D806,117 | S | 12/2017 | Springer |
| D806,118 | S | 12/2017 | Durrant et al. |
| D806,718 | S | 1/2018 | Yang |
| D809,006 | S | 1/2018 | Mehta et al. |
| 2002/0163538 | A1 | 11/2002 | Shteyn |
| 2004/0147840 | A1 | 7/2004 | Duggirala et al. |
| 2005/0285853 | A1 | 12/2005 | Morita et al. |
| 2007/0124677 | A1 | 5/2007 | de los Reyes et al. |
| 2007/0177782 | A1 | 8/2007 | Raffy |
| 2009/0024030 | A1 | 1/2009 | Lachaine et al. |
| 2009/0226063 | A1 | 9/2009 | Rangwala et al. |
| 2011/0182493 | A1* | 7/2011 | Huber .............. G16H 15/00 382/132 |
| 2011/0268338 | A1 | 11/2011 | Collins et al. |
| 2012/0130223 | A1* | 5/2012 | Reicher .............. G06F 19/321 600/407 |
| 2013/0290826 | A1 | 10/2013 | Niwa et al. |
| 2013/0343626 | A1 | 12/2013 | Rico et al. |
| 2014/0108983 | A1 | 4/2014 | William R. et al. |
| 2014/0149407 | A1 | 5/2014 | Qian et al. |
| 2014/0181128 | A1 | 6/2014 | Riskin et al. |
| 2014/0233814 | A1 | 8/2014 | Ikeda |
| 2015/0089337 | A1* | 3/2015 | Grady .............. G06T 19/00 715/202 |
| 2015/0261915 | A1* | 9/2015 | Yanagida .............. G06F 19/321 382/131 |
| 2015/0262014 | A1* | 9/2015 | Iwamura .............. G06K 9/6253 382/128 |
| 2016/0103816 | A1 | 4/2016 | Grady et al. |
| 2016/0314246 | A1* | 10/2016 | Roberge .............. G06F 19/321 |
| 2017/0358075 | A1 | 12/2017 | Cao et al. |
| 2018/0046758 | A1 | 2/2018 | Gogin et al. |

FOREIGN PATENT DOCUMENTS

| | | |
|---|---|---|
| CN | 104933288 A | 9/2015 |
| WO | 2015173675 A1 | 11/2015 |

OTHER PUBLICATIONS

Office Action from the U.S. Patent and Trademark Office for U.S. Appl. No. 15/253,764 dated Dec. 12, 2017 (15 pages).
Office Action from the U.S. Patent and Trademark Office for U.S. Appl. No. 29/603,893 dated Mar. 8, 2018 (10 pages).
Office Action from the U.S. Patent and Trademark Office for U.S. Appl. No. 29/603,891 dated Mar. 5, 2018 (6 pages).
Office Action from the U.S. Patent and Trademark Office for U.S. Appl. No. 29/603,887 dated Mar. 5, 2018 (6 pages).
Office Action from the U.S. Patent and Trademark Office for U.S. Appl. No. 29/603,888 dated Mar. 5, 2018 (7 pages).
Office Action from the U.S. Patent and Trademark Office for U.S. Appl. No. 29/603,889 dated Mar. 5, 2018 (7 pages).
Yang, J. et al.; "Method and Apparatus for Evaluating the Quality of Medical Imaging Systems and Components Using Model Observers and Computer Aided Detection Algorithms"; http://ip.com/IPCOM/000130693D; Nov. 1, 2005.
Anonymously; "Methods of Providing Translucent Annotations in Medical Images"; http://ip.com/IPCOM/000152706D; May 10, 2007.
Donner, R. et al.; "One-shot learning of anatomical structure localization models"; 2013 IEEE 10th International Symposium on Biomedical Imaging: From Nano to Macro(ISBI 2013), pp. 222-225. IEEE; 2013.
Non-Final Office Action from the U.S. Patent and Trademark Office for U.S. Appl. No. 29/603,887 dated Jun. 29, 2018 (7 pages).
Yay Media AS, "Minus sign icon" Oct. 19, 2015 http://www.alamy.com/ stock-photo-minus-sign-icon-negative-symbol-zoom-out-seamless-pattern-on-a-gray-115998951.html.
Non-Final Office Action from the U.S. Patent and Trademark Office for U.S. Appl. No. 29/603,889 dated Jun. 29, 2018 (5 pages).
Non-Final Office Action from the U.S. Patent and Trademark Office for U.S. Appl. No. 29/603,888 dated Jun. 29, 2018 (9 pp.).
Final Office Action from the U.S. Patent and Trademark Office for U.S. Appl. No. 29/603,893 dated Nov. 15, 2018 (6 pages).
Non-Final Office Action from the U.S. Patent and Trademark Office for U.S. Appl. No. 15/253,764 dated Aug. 8, 2018 (17 pages).
Non-Final Office Action from the U.S. Patent and Trademark Office for U.S. Appl. No. 29/603,888 dated Jun. 29, 2018 (9 pages).
Non-Final Office Action from the U.S. Patent and Trademark Office for U.S. Appl. No. 15/253,755 dated Sep. 5, 2018 (13 pages).
Non-Final Office Action from the U.S. Patent and Trademark Office for U.S. Appl. No. 29/603,891 dated Aug. 31, 2018 (8 pages).
Jay, "InfoPath 2007/2010>>Drop Down List", May 17, 2011, https://rayamondo.wordpress.com/2011/05/17/infopath-setting-drop-down-lists/, (6 pages).
Aug. 31, 2016, U.S. Appl. No. 15/253,746, US2018/0060533.
Aug. 31, 2016, U.S. Appl. No. 15/253,752, US2018/0060534.
Aug. 31, 2016, U.S. Appl. No. 15/253,755, US2018/0055468.
Aug. 31, 2016, U.S. Appl. No. 15/253,760, US2018/0060535.
Aug. 31, 2016, U.S. Appl. No. 15/253,764, US20180060488.
May 12, 2017, U.S. Appl. No. 29/603,887.
May 12, 2017, U.S. Appl. No. 29/603,888.
May 12, 2017, U.S. Appl. No. 29/603,889.
May 12, 2017, U.S. Appl. No. 29/603,891.
May 12, 2017, U.S. Appl. No. 29/603,893.
Non-Final Office Action from the U.S. Patent and Trademark Office for U.S. Appl. No. 15/253,752 dated Sep. 19, 2018 (26 pages).
Non-Final Office Action from the U.S. Patent and Trademark Office for U.S. Appl. No. 15/253,760 dated Sep. 21,2018 (21 pages).
Final Office Action from the U.S. Patent and Trademark Office for U.S. Appl. No. 29/603,888 dated Dec. 14, 2018 (6 pages).
Notice of Allowance from the U.S. Patent and Trademark Office for U.S. Appl. No. 15/253,746 dated Dec. 11, 2018 (9 pages).
Final Office Action from the U.S. Patent and Trademark Office for U.S. Appl. No. 15/253,755 dated Jan. 11, 2019 (13 pages).
Final Office Action from the U.S. Patent and Trademark Office for U.S. Appl. No. 15/253,764 dated Dec. 10, 2018 (18 pages).
Ex Parte Quayle Action from the U.S. Patent and Trademark Office for U.S. Appl. No. 29/603,889 dated Jan. 11, 2019 (4 pages).
Non-Final Office Action from the U.S. Patent and Trademark Office for U.S. Appl. No. 29/603,891 dated Mar. 4, 2019 (7 pages).

(56) References Cited

OTHER PUBLICATIONS

"Dita Repository" Jun. 20, 2010 http://www.siberlogic.com/features/dita_features/dita_repository.html.

* cited by examiner

PROCEDURE: BILATERAL SCREENING DIGITAL MAMMOGRAM WITH BREAST IMPLANTS WITH COMPUTER-AIDED DETECTION

COMPARISON: DRS Hospital #5, MG, MAMMO SCREENING W IMPLANTS BILATERAL, Jun-28-11, 00:00.

INDICATIONS: Screening.

FIVE YEAR BREAST CANCER % RISK: 1.60%
LIFETIME BREAST CANCER % RISK: 7.50%
CALCULATOR: NCI Breast Cancer Risk Assessment Tool
PERSONAL BREAST CANCER: No
PERSONAL OVARIAN CANCER: No
TREATMENTS: None
FAMILY CANCERS: Cousin-paternal with breast cancer at age 34;
Grandmother-paternal with prostate cancer at age 54.

BREAST COMPOSITION:

FINDINGS:

RECOMMENDATIONS:

FIG. 10

AUTOMATED ANATOMICALLY-BASED REPORTING OF MEDICAL IMAGES VIA IMAGE ANNOTATION

BACKGROUND

Embodiments of the present invention relate to automatically populating a structured report for medical data, and more specifically, to mapping image annotations to data fields of a structured report.

SUMMARY

A reviewing physician ("reader") generates a report as part of an image study (for example, a cardiology report, ultrasound report, and the like). Structured reporting software applications allow a reader to generate a structured report. For example, a structured reporting software application may provide a menu of available report data elements that a reader may select and then populate the selected data elements with values. The menu of available data elements or sections is commonly structured as a tree structure, where a reader drill-downs from a high-level report type to specific data elements. Using such a tree structure involves a lot of user interaction with the software application (for example, mouse clicks) that may interrupt the reader from viewing the data (for example, images) that he or she is reporting on.

Therefore, embodiments of the invention provide methods and systems for reviewing medical images and generating a report for a medical image. One embodiment of the invention provides a method of generating an electronic structured report associated with a displayed electronic medical image. The method includes receiving an annotation for the electronic medical image, automatically determining, with an electronic processor, an anatomical location within the electronic medical image associated with the annotation, and automatically determining, with the electronic processor, a location within the electronic structured report associated with the anatomical location based on a predetermined mapping. The method also includes automatically populating the location of the electronic structured report based on the annotation. The electronic structured report may be anatomically-structured. Also, the annotation may include a label that is transferred to the location of the electronic structured report. Also, in some embodiments, an anatomical location syntax associated with the annotation is generated and wherein automatically populating the location of the electronic structured report based on the annotation includes populating the location with at least one value included in the anatomical location syntax.

Another embodiment of the invention provides a system including an electronic processor. The electronic processor is configured to display an electronic medical image, receive an annotation for the electronic medical image, automatically determine an anatomical location within the medical image associated with the annotation, and automatically determine a location within an electronic structured report associated with the anatomical location based on a predetermined mapping. The electronic processor is also configured to automatically populate the location of the electronic structured report based on the annotation, and automatically output data to a reader of the electronic medical image informing the reader of the location of the electronic structured report, wherein the output data includes at least one of visual data and audio data.

An additional embodiment of the invention provides non-transitory computer-readable medium including instructions that, when executed by an electronic processor, cause the electronic processor to perform a set of functions. The set of functions includes receiving a first annotation for a medical image, automatically determining a location within an electronic structured report associated with the first annotation based on a predetermined mapping, and automatically populating the location of the electronic structured report based on the first annotation. The set of functions also includes updating the first annotation displayed within the medical image to display the first annotation in a first manner different from a second manner used to display a second annotation within the medical image not mapped to any location within the electronic structured report. Updating the first annotation may include updating a color of the first annotation, a size of the first annotation, an animation of the first annotation, a graphic of the first annotation, or a combination thereof.

Another embodiment of the invention provides a system for reviewing medical images. The system includes an electronic processor configured to receive an annotation for a displayed electronic medical image, wherein the annotation includes a label of a lesion represented within the medical image, and automatically determine whether the lesion is labeled one or more times in other medical images acquired during an imaging exam associated with the displayed electronic medical image. The electronic processor is further configured to identify a stored rule based on the annotation, wherein the stored rule specifies whether the lesion should be labeled in the other medical images, and execute the stored rule based on whether the lesion is labeled one or more times in the other medical images. The electronic processor is also configured to automatically initiate at least one automatic action based on executing the stored rule. The at least one automatic action may include generating a warning, updating the annotation, or performing a combination thereof. The label may identify the lesion as a mass and the stored rule may be associated with a reader, a workstation, an organization, an application, a patient, an image modality, an anatomical structure, the medical image, or a combination thereof Yet another embodiment of the invention provides non-transitory computer-readable medium including instructions that, when executed by an electronic processor, cause the electronic processor to perform a set of functions. The set of functions includes receiving a first annotation for a first electronic medical image, wherein the first annotation includes a label of a lesion represented within the first medical image, and receiving a second annotation for a second electronic medical image, wherein the second annotation includes a label of the lesion represented within the first medical image. The set of functions also includes identifying a stored rule based on at least one of the first annotation and the second annotation, executing the stored rule based on the first annotation and the second annotation, and automatically updating at least one of the first annotation and the second annotation based on executing the stored rule. In some embodiments, the first annotation, the second annotation, or both are updated to designate the lesion as a mass.

A further embodiment of the invention provides a method of reviewing medical images. The method includes receiving a first annotation for a first electronic medical image marking a first anatomical location, wherein the first medical image represents an anatomical structure from a first view, and receiving a second annotation for a second electronic medical image marking a second anatomical location, wherein the second medical image represents the anatomical structure from a second view. The method also includes automatically determining, with an electronic processor, a third anatomical location within the second medical image based on the first annotation, comparing, with the electronic processor, the third anatomical location to the second anatomical location, and automatically initiating, with the electronic processor, at least one automated action in response to the second anatomical location being inconsistent with the third anatomical location. The at least one automated action may include generating a warning indicating a degree of match between the third anatomical location and the second anatomical location.

Another embodiment of the invention provides a system for reviewing medical images. The system includes an electronic processor configured to create a data structure for tracking anatomical findings, receive a first annotation marking a first anatomical finding within a first electronic medical image, wherein the first electronic medical image was captured during a first imaging procedure of an anatomical structure, and add data to the data structure representing a first parameter of the first anatomical finding. The electronic processor is also configured to receive a second annotation marking a second anatomical finding within a second electronic medical image, wherein the second electronic medical image was captured during a second imaging procedure of the anatomical structure, and add data to the data structure representing a second parameter of the second anatomical finding. The electronic processor is also configured to display at least a portion of the data structure. The data added to the data structure may represent a size, a location, or both of an anatomical finding. The electronic processor may also be configured to superimpose an identifier of a clinical event on the displayed data structure. Other embodiments of invention provide non-transitory computer-readable medium including instructions that, when executed by an electronic processor, cause the electronic processor to perform the above functionality.

A further embodiment of the invention provides a method of reviewing medical images. The method includes creating a data structure for tracking anatomical findings, receiving a first annotation marking a first anatomical finding associated with an image study, and adding a first parameter of the first anatomical finding to the data structure. The method also includes receiving a second annotation marking a second anatomical finding associated with the image study, and adding a second parameter of the second anatomical finding to the data structure. In addition, the method includes displaying data based on the data structure. The displayed data may indicate a number of lesions marked within an image study or an image or may include an indicator of whether any lesions are marked within the image study.

Yet another embodiment of the invention provides a system for reviewing medical images. The system includes an electronic processor configured to display an electronic medical image, compile clinical information associated with the electronic medical image, determine a probability of a condition associated with a patient associated with the electronic medical image based on the clinical information, and display the probability of the condition with the medical image. The electronic processor is also configured to receive an annotation for the electronic medical image, determine an updated probability of the condition based on the clinical information and the annotation, and display the updated probability of the condition. In some embodiments, the electronic processor is configured to determine the updated probability of the condition based on at least one rule associated with at least one selected from a group consisting of a geographic location, an organization, a reader, a referring physician, and a patient. The electronic processor may also be configured to display the updated probability using at least one selected from a group consisting of a colored highlight, a flashing signal, and a tone. Additional embodiments of the invention provide a method and computer-readable medium including instructions that when executed by an electronic processor perform the above functionality.

Another embodiment of the invention provides a system for manually annotating medical images. The system includes an electronic processor configured to receive, through an input mechanism, a selection of a mark (for example, a shape), receive, through the input mechanism, a selection of an annotation type associated with the mark, and store a mapping of the mark to the annotation type. The electronic processor is also configured to receive an annotation for a displayed electronic medical image, wherein the annotation includes the mark, and automatically update, based on the mapping, the annotation based on the annotation type. Other embodiments of the invention provide non-transitory computer-readable medium including instructions that, when executed by an electronic processor, cause the electronic processor to perform the above functionality.

A further embodiment of the invention provides a method for annotating medical images. The method includes displaying an electronic medical image, receiving an annotation for the electronic medical image, and identifying, with an electronic processor, a stored rule based on the annotation, the stored rule specifying whether one or more values should be automatically generated for the annotation. The method also includes executing, with the electronic processor, the stored rule based on the annotation, and automatically modifying, with the electronic processor, the annotation based on executing the stored rule. The stored rule may be identified based on a reader assigned to the electronic medical image, an imaging site, a reading site, an exam type of the electronic medical image, an anatomical structure represented in the electronic medical image, an anatomical structure associated with the annotation, or a combination thereof. The annotation may be automatically modified by automatically determining a value for the annotation based on the electronic medical image.

BRIEF DESCRIPTION OF THE DRAWINGS

FIG. 10 illustrates a sample portion of a partially-completed mammogram report.

DETAILED DESCRIPTION

Figure 1:
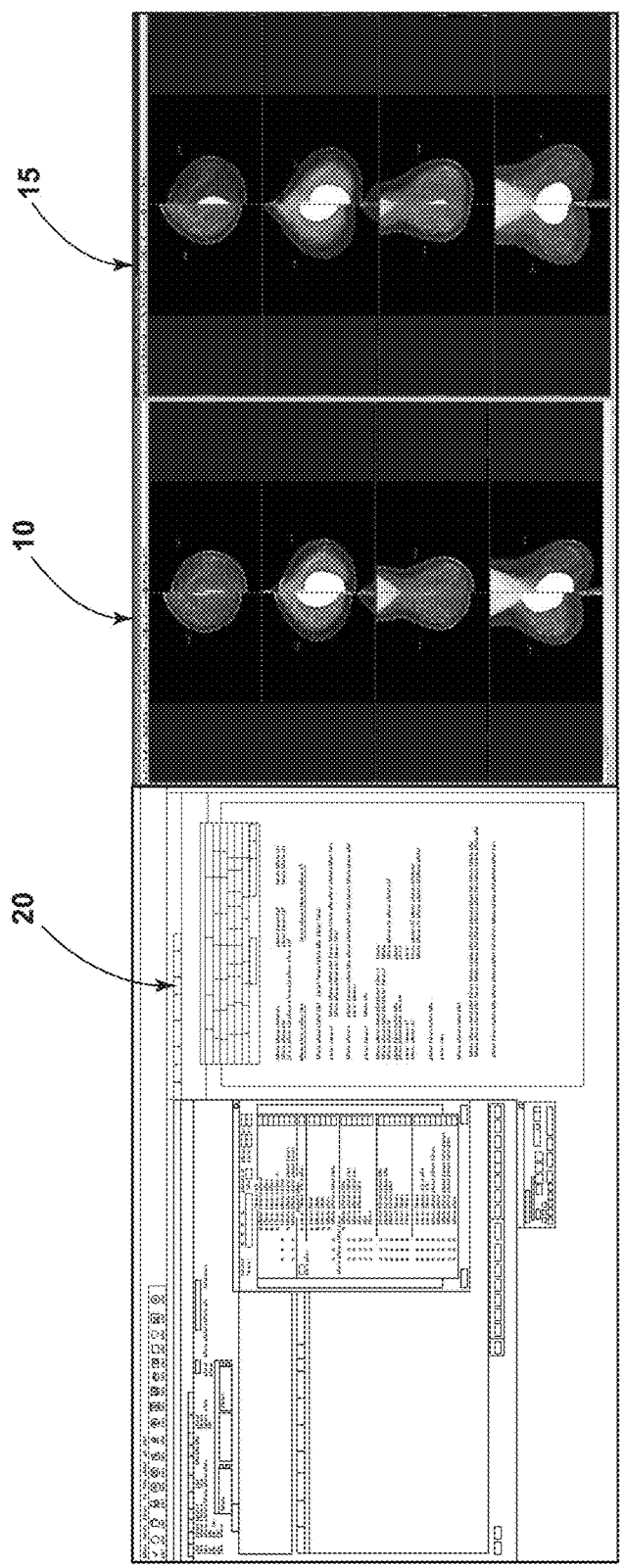
FIG. 1 illustrates example information displayed to a reading physician.

When a reading physician (a "reader") reads an imaging examination (for example, a mammogram) using a conventional computerized reading and reporting system, the reporting system may display, for example, as illustrated in FIG. 1, an electronic medical images from a current exam 10 and one or more relevant prior exams 15. Alternatively or in addition, the reporting system may display a patient's clinical information, a current clinical report, one or more prior clinical reports, various electronic forms, a computer-aided detection (CAD) structured report, and one or more dialogs for coding a finding, reporting the finding, or both in accordance with Mammography Quality Standards Act (MQSA) requirements and the American College of Radiology (ACR) Breast Imaging-Reporting and Data System (BI-RADS®) guidelines.

The reporting system may display the current exam 10, relevant prior exams 15, or a combination thereof using a variety of manually-selected or automatically-selected display protocols. For example, as illustrated in FIG. 1, the current exam 10, which includes eight medical images, may be displayed to the left of the relevant one or more prior exams 15, which also includes eight images.

Although there are variations in the behavior of each individual reading physician, the review process generally starts with the reader checking the patient's relevant history and risk factors. Checking the patient's relevant history and risk factors may involve multiple steps, such as opening electronic documents, collecting paper documents, and the like. In some embodiments, as illustrated in FIG. 1, the patient's relevant history and risk factors may be automatically compiled and presented in, for example, a pre-processed clinical report 20. The pre-processed clinical report 20 may allow the reader to gain a faster understanding of, for example, the patient's information and the information provided by the patient's referring doctor.

After checking the patient's relevant history and risk factors, the reader generally proceeds with viewing the patient's clinical images (for example, the images included in the current exam 10). The reader may view the patient's clinical images on one or more computer monitors approved for digital mammography by the Food and Drug Administration (FDA). While viewing the patient's clinical images, the reader may rearrange the images multiple times to compare images of the same exam, compare images from the current exam 10 to images from the relevant one or more prior exams 15, or a combination thereof. The arrangement and presentation of the images may be controlled by, for example, personal preferences. For example, the reader may use input mechanisms (for example, a keyboard, a mouse, a microphone, and the like) to progress through a series of display protocols. Furthermore, the reader may elect to magnify the images, display computer-aided diagnosis (CAD) marks, or a combination thereof. Alternatively or in addition, the reader may elect to display minified views of the images (for example, image thumbnails) to facilitate dragging and dropping of images in various display locations.

After the reading physician completes his or her review of the patient's clinical images, the reader generates a report for the current exam 10 by, for example, dictation, speech recognition, typing, mouse clicks upon one or more dialogs (for example, various user interfaces enabling text input into a report, ranging from dictation to mouse-driven data input forms), or a combination thereof. Accordingly, readers often divide time between gaining an understanding of a patient's clinical condition and risks, viewing image, and generating a report and often need to change their focus and interaction between numerous interfaces and displays to complete a report. This interaction may be inefficient and may introduce errors.

Accordingly, embodiments of the present invention use image analytics, deep learning, artificial intelligence, cognitive science, or a combination thereof to improve reader performance. For example, as described in more detail below, embodiments of the invention allow a reader to click on an electronic displayed medical image (for example, a mammogram or other type of digitally-displayed medical image) and automatically populate a report, which may substantially reduce reporting time, improve adherence to established reporting standards (such as ACR BI-RADS®), and reduce some common errors (for example, the reader seeing a lesion in the left breast and erroneously stating that the lesion is in the right breast).

Figure 2:
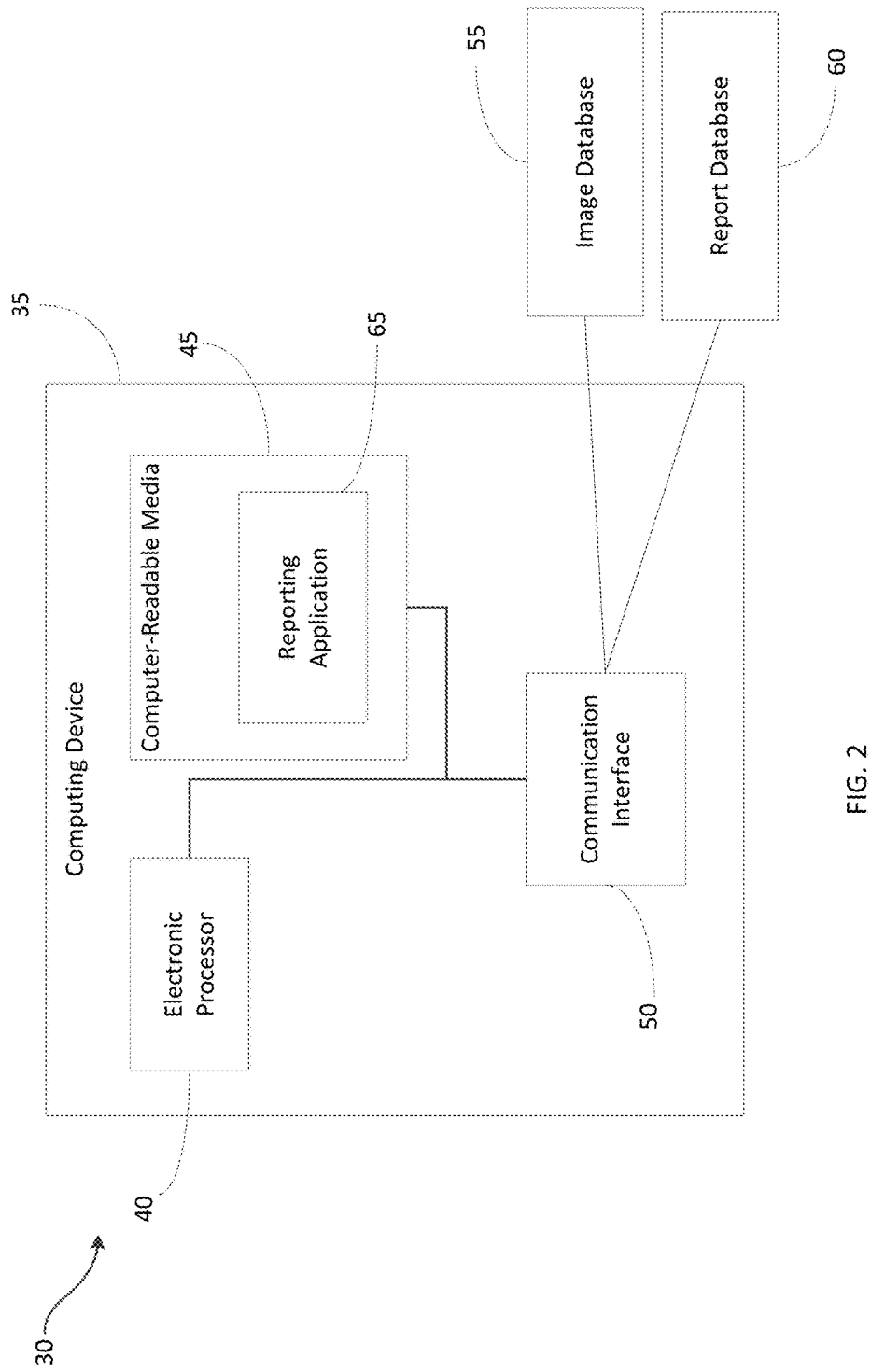
FIG. 2 schematically illustrates a system for generating a report.

For example, FIG. 2 schematically illustrates a system 30 for generating a report. As shown in FIG. 2, the system 30 includes a computing device 35 including an electronic processor 40, a non-transitory computer-readable medium 45, and a communication interface 50. Although, the electronic processor 40, the computer-readable medium 45, and the communication interface 50 are illustrated as part of a single computing device 35 (for example, such as a personal computer or a server), the components of the computing device 35 may be distributed over multiple computing devices 12. Similarly, the computing device 35 may include multiple electronic processors, computer-readable medium modules, and communication interfaces and may include additional components than those illustrated in FIG. 2.

The electronic processor 40 retrieves and executes instructions stored in the computer-readable medium 45. The electronic processor 40 may also store data to the computer-readable medium 45. The computer-readable medium 45 may include non-transitory computer readable medium and may include volatile memory, non-volatile memory, or combinations thereof. In some embodiments, the computer-readable medium 45 includes a disk drive or other types of large capacity storage mechanisms.

The communication interface 50 receives information from data sources external to the computing device 35 and outputs information from the computing device 35 to external data sources. For example, the communication interface 50 may include a network interface, such as an Ethernet card or a wireless network card that allows the computing device 35 to send and receive information over a network, such as a local area network or the Internet. As illustrated in FIG. 2, in some embodiments, the communication interface 50 communicates (directly or indirectly) with an image database 55 and a report database 60. As described in more detail below, the image database 55 may store patient information, including images, patient identifiers, patient history, order information, and the like. The report database 60 stores reports, such as structured image study reports. In some embodiments, the image database 55 and the report database 60 are combined in a single database. In other embodiments, the image database 55, the report database 60, or a combination thereof are distributed over multiple databases. Also, in some embodiments, the image database 55, the report database 60, or both are included within the computing device 35 (for example, as part of the computer-readable medium 45). In some embodiments, the computing device 35 also includes drivers configured to receive and send data to and from one or more peripheral devices (for example, input mechanisms and output mechanisms), such as a keyboard, a mouse, a printer, a microphone, a monitor, and the like.

The instructions stored in the computer-readable medium 45 perform particular functionality when executed by the electronic processor 40. For example, as illustrated in FIG. 2, the computer-readable medium 45 includes a reporting application 65. As described in more detail below, the reporting application 65, when executed by the electronic processor 40, generates reports, such as a structured report for a medical image study (for example, a mammogram, a cardiology report, ultrasound report, and the like). In some embodiments, in addition to providing reporting functionality, the reporting application 65 provides functionality for viewing medical images, accessing patient information, or a combination thereof.

In some embodiments, the computing device 35 is a personal computer operated by a reader to locally execute the reporting application 65. However, in other embodiments, the computing device 35 is a server that hosts the reporting application 65 as a network-based application. Therefore, a reader may access the reporting application 65 through a communication network, such as the Internet. Accordingly, in some embodiments, a reader is not required to have the reporting application 65 installed on their workstation or personal computer. Rather, in some embodiments, the reader may access the reporting application 65 using a browser application, such as Internet Explorer® or FireFox®.

In some embodiments, the reporting application 65 interacts with the image database 55 to access images, generates a report based on the images (for example, based on input from a reader), and stores the generated report to the report database 60. In some embodiments, the image database 55, the report database 60, or a combination thereof, are included in a picture archiving and communication system (PACS). Also, in some embodiments, the computing device 35 is included in a PACS. In other embodiments, the computing device 35 may access the image database 55, the report database 60, and other components of a PACS through the communication interface 50.

Figure 3:
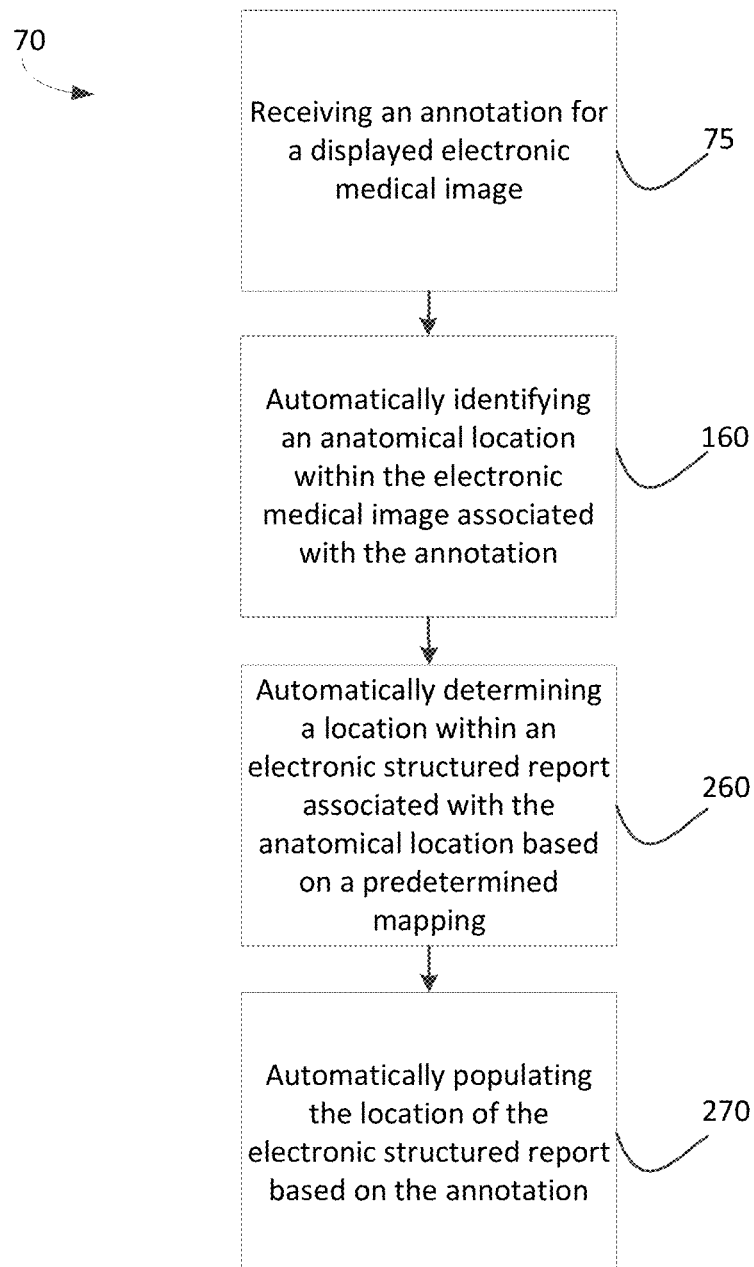
FIG. 3 is a flow chart illustrating a method of generating a report performed using the system of FIG. 2.

FIG. 3 illustrates a method 70 performed by the system 30 for generating a report for a medical image. The method 70 is described below as being performed by the reporting application 65 (as executed by the electronic processor 40). However, the method 70 or portions thereof may be performed by one or more separate software applications (executed by the electronic processor 40 or one or more other electronic processors) that interact with the reporting application 65 (for example, as add-on functionality).

As illustrated in FIG. 3, when an electronic medical image is displayed (for example, by the reporting application 65 or a separate viewing application), the method 70 includes receiving an annotation for the medical image (at block 75). The annotation represents an electronic selection of a particular location within the displayed electronic medical image and may be associated with one or more values, such as a label, a measurement, a finding, and the like. As used in the present application, an annotation may also be referred to as a "marktation." An annotation may take various shapes (such as, for example, circles, arrows, lines, rectangles, spheres, and the like), sizes, and forms and may be a one-dimensional mark, a two-dimensional mark, or a three-dimensional mark. In some embodiments, the reporting application 65 include one more tools for adding an annotation to a displayed medical image, such as a toolbar that includes icons associated with different shapes and sizes of marks that a reader can select (drag and drop) and add to a displayed image.

Figure 4:
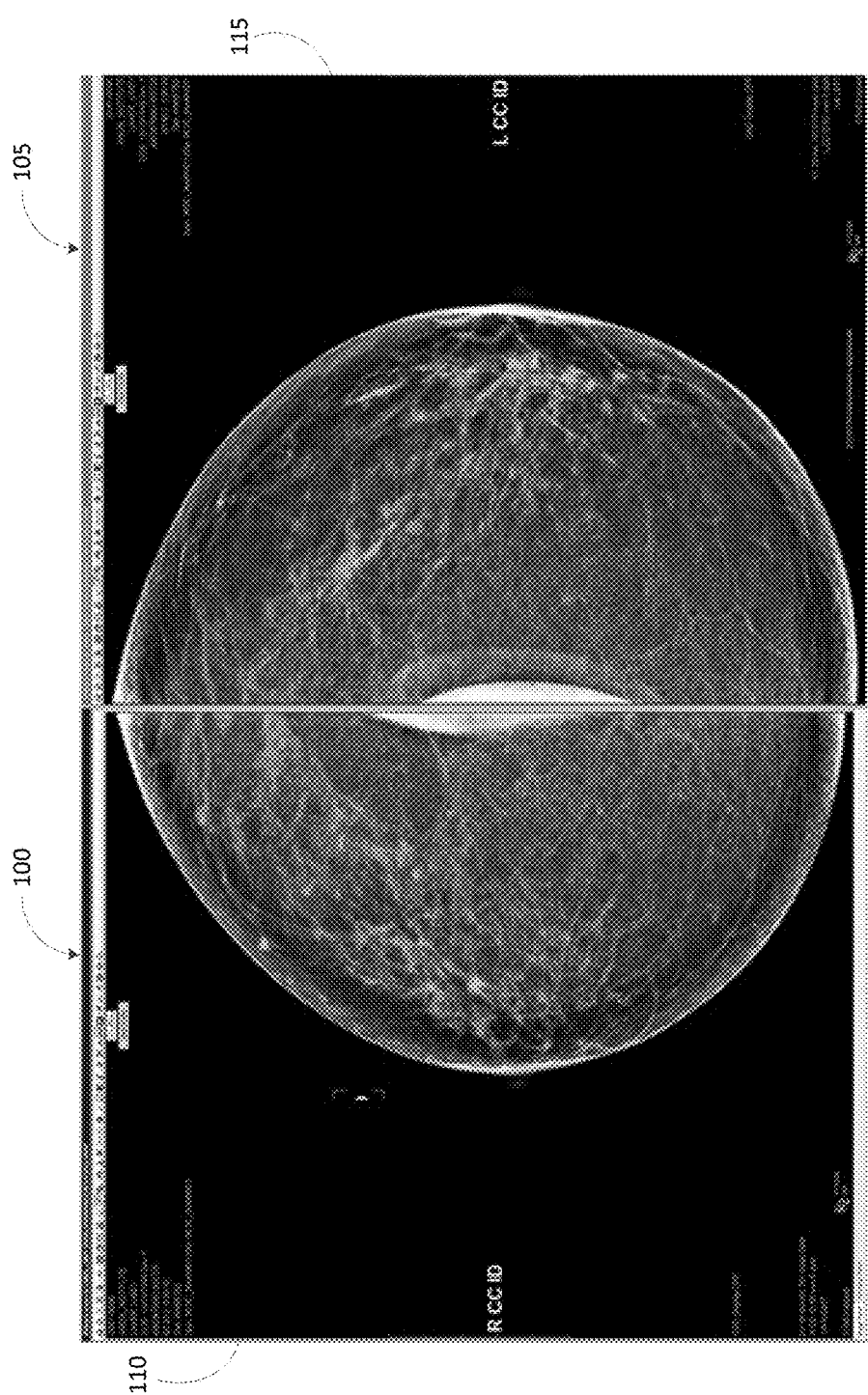
FIG. 4 illustrates a right bilateral craniocaudal mammogram view and a left bilateral craniocaudal mammogram view displayed in a back-to-back orientation.

In some embodiments, the reporting application 65 also provides one or more tools or automated functionality to aid a reader in generating an annotation. For example, in some embodiments, the reporting application 65 automatically scales the medical image displayed to the reader. As one example, FIG. 4 illustrates a left bilateral craniocaudal mammogram view 100 and a right bilateral craniocaudal mammogram view 105. The left bilateral craniocaudal mammogram view 100 and the right bilateral craniocaudal mammogram view 105 are displayed with a back-to-back orientation. The right bilateral craniocaudal mammogram view 105 is positioned within a first display container 110 and the left bilateral craniocaudal mammogram view 100 is positioned within a second display container 115. The reporting application 65 may automatically expand each bilateral craniocaudal mammogram view 100 and 105 into each of the respective display containers 110 and 115. For example, as illustrated in FIG. 4, the reporting application 65 may be configured to automatically expand each of the bilateral craniocaudal mammogram views 100 and 105 to fit within each of the respective display containers 110 and 115 without cutting off relevant portions of an anatomical structure represented in the views. The reporting application 65 may perform such automated scaling using image analytics, a computer algorithm that assesses the contour of the breast to facilitate the automated magnification and displays of each of the bilateral craniocaudal mammogram views 100 and 105, or a combination thereof.

Figure 5:
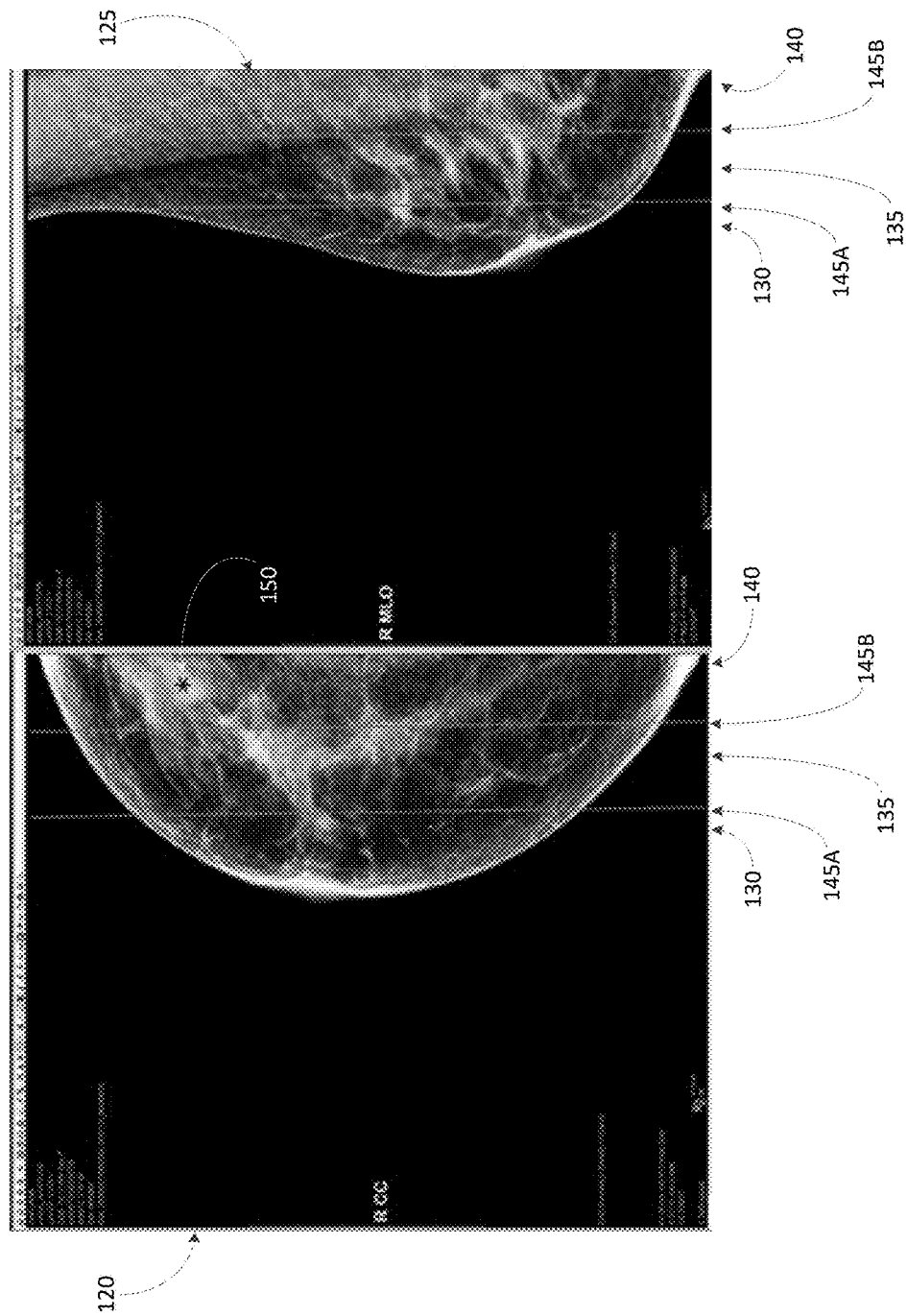
FIG. 5 illustrates a right craniocaudal mammogram view and a mediolateral oblique mammogram view with a depth graphic dividing each breast into anterior, middle, and posterior thirds.

In some embodiments, the reporting application 65 also automatically divides an anatomical structure represented in a medical image to one or more image depths. For example, for a mammogram, the reporting application 65 may automatically detect a breast contour and divide each breast into multiple (for example, three) anatomical depths, such as an anterior depth, a middle depth, and a posterior depth. The reporting application 65 may perform the divisions by dividing a distance from an areola to a chest wall by the number of desired depths. For example, FIG. 5 illustrates a right craniocaudal mammogram view 120 and a right mediolateral mammogram view 125. Each mammogram view 120 and 125 is divided into an anterior depth 130, a middle depth 135, and a posterior depth 140. In some embodiments, there may be additional or fewer anatomical depths based on different anatomical landmarks. Also, although mammograms are used for many of the examples provided in the present application, the methods and systems described herein may be used with different types of medical images for different types of anatomical structures generated using various types of imaging modalities, including but not limited to a magnetic resonance imaging (MRI) scan, a position emission tomography (PET) scan, an x-ray computed tomography (CT) scan, a nuclear medicine (NM) scan, a computed radiography (CR) scan, an x-ray angiography (XA) scan, a breast tomosynthesis, and other modalities as defined by the Digital Imaging and Communications in Medicine (DICOM) standard.

Optionally, the reporting application 65 may automatically display one or more depth graphics 145 based on the depth divisions. For example, as illustrated in FIG. 5, each mammogram view 120 and 125 includes a first depth graphic 145A positioned between the anterior depth 130 and the middle depth 135 and a second depth graphic 145B positioned between the middle depth 135 and the posterior depth 140. In some embodiments, the one or more depth graphics 145 automatically appear when the reader interacts with the medical image. For example, the one or more depth graphics 145 may transiently appear when the reader is annotating the medical image (for example, to mark a lesion). Alternatively or in addition, the one or more depth graphics 145 may appear when the reader activates a microphone used to dictate a finding.

Figure 6:
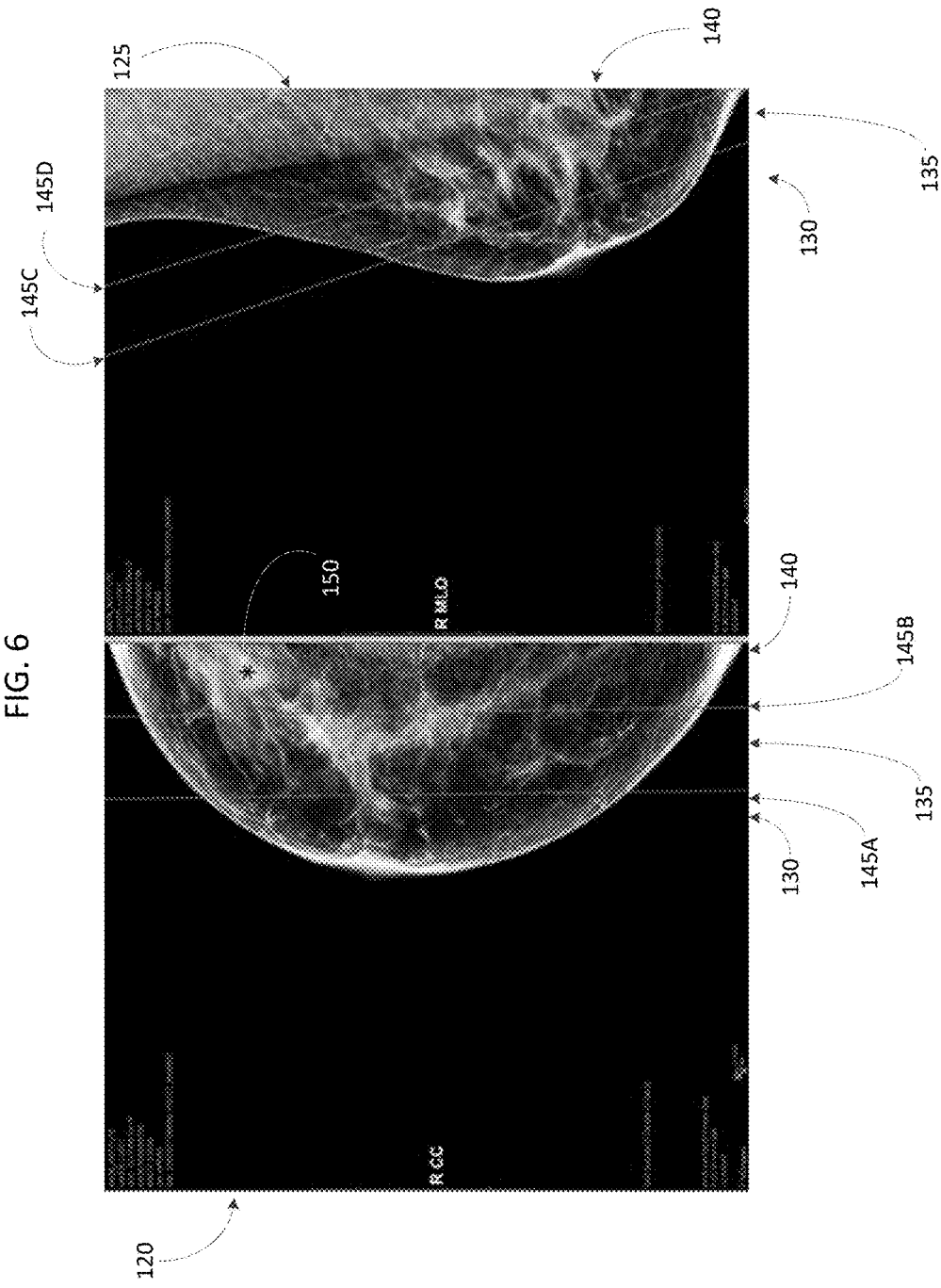
FIG. 6 illustrates a right craniocaudal mammogram view and a mediolateral oblique mammogram view with a depth graphic dividing each breast into anterior, middle, and posterior thirds with the divisions on the oblique image shown as oblique lines.

When a breast is imaged in the oblique plane, the actual depth of an anatomical point relative to the areola depends on the obliquity of the image. Therefore, unlike the right mediolateral mammogram view 125 illustrated in FIG. 5, the anatomical depth may be more on an oblique mammography projection. Therefore, the anatomical depth may be more accurately depicted as illustrated in FIG. 6. As illustrated in FIG. 6, the one or more depth graphics 145 on the right mediolateral mammogram view 125 may be illustrated as a first oblique line 145C positioned between the anterior depth 130 and the middle depth 135 and a second oblique line 145D positioned between the middle depth 135 and the posterior depth 140.

In some embodiments, the reporting application 65 determines the angle of the first oblique line 145C and the angle of the second oblique line 145D based on information stored in a Digital Imaging and Communications in Medicine (DICOM) meta-file associated with the displayed medical image (for example, stored in the image database 55). The information in the DICOM meta-file may indicate the obliquity of the imaging system when the image was obtained. The reader may also manually adjust the obliquity of the position of the first oblique line 145C and the second oblique line 145D. In some embodiments, the reporting application 65 assesses the DICOM meta-file, other image obliquity information, or both to automatically create anatomical graphics and divisions.

In addition to or as an alternative to the depth graphics 145, in some embodiments, the reporting application 65 automatically generates and displays one or more labels within the medical image. The labels identify the position of particular anatomical locations or landmarks within the medical image. For example, for a mammogram, the reporting application 65 may display labels for an areoloar position, a subreolar position, a dermal position, a subdermal position, a subcutaneous position, an axillary position, a chest wall position, an implant position, or a combination thereof. The reporting application 65 may automatically generate the labels using one or more types of image analytics including, for example, assessment of skin contours, density, MRI intensity, vascular enhancement patters, segmentation of images tissues, or a combination thereof. In some embodiments, the reporting application 65 may refine the automatic labeling based on artificial intelligence and deep learning (for example, tracking where manual labels are positioned or how automatically-generated labels are manually adjusted). As described below, the automated labels may be used an annotations. However, they may also be used to provide overall knowledge of anatomic location, which assists a reader in viewing and understanding an image.

In some embodiments, the reader manually controls the display of the one or more depth graphics 145, the labels, or both using, for example, an audio command, a mouse click, a keyboard shortcut, or a combination thereof. Furthermore, the reader may interactively adjust the position of the one or more divisions, depth graphics 145, labels, or both. For example, in some embodiments, the reader may manually adjust the position a depth graphic 145 included in an image of a breast with a post-operative or congenital deformity.

Also, in some embodiments, the reporting application 65 generates and displays the one or more depth graphics 145, the labels, or both based on configurable rules. The rules may be based on reader preferences, site administrator settings, or both. Alternatively or in addition, the rules may be based on an imaging modality associated with the displayed medical image, one or more patient characteristics associated with the displayed medical image, one or more reader characteristics associated with the displayed medical image, or a combination thereof. For example, certain labels may be used for an MRI scan while other labels may be used for a mammogram. The rules may also be based on a patient's risk for having a particular condition, an imaged body region (for example, a body part), or a combination thereof. In general, the rules may be based on a workstation where the medical image is displayed, an organization, a facility, a location, an imaging modality, a patient, a referring doctor, one or more reading physician characteristics, or a combination thereof.

Rules may also be used to specify what graphics, labels, or both are displayed based on where a cursor is positioned within a displayed image. For example, when viewing a CT scan of the abdomen, anatomical graphics and labels related to the liver may be accessible, automatically appear, be employed, or a combination thereof when the cursor is placed over the liver, which may be different than the anatomical graphics and labels that may be accessible, automatically appear, be employed, or a combination thereof when the cursor is placed over the kidney.

A reader may provide an annotation manually. For example, a reader may mark a location on a displayed image (for example, by clicking on a location) and provide one or more values associated with the location, such as a label, a finding, a measurement, a note, and the like. The reader may use the displayed depth graphics 145, labels, or both to determine a location to mark. Alternatively or in addition, a reader may generate an annotation by selecting a label displayed within the medical image. Similar to manually-marked annotations, the reader may provide a value for the annotation that includes a label, a measurement, a finding, a note, or a combination thereof. Also, in some embodiments, the reporting application 65 may be configured to automatically generate one or more values for an annotation. For example, in some embodiments, when a reader manually marks a lesion within a displayed image or selects an automatically-generated label identifying a lesion, the reporting application 65 may be configured to automatically identify an anatomical position of the marked location, characterize the lesion, measure the lesion, or a combination thereof. In some embodiments, any automated values are displayed to the reader for acceptance, rejection, or editing.

For example, when the reader uses an input mechanism, such as keyboard, a mouse, a joystick, or the like to control a cursor to mark a lesion within a displayed image, the reporting application 65 generates information related to the location of the marked lesion (for example, a depth). In particular, as illustrated in FIG. 5, an annotation 150 (illustrated as an asterisk) marks a lesion in the posterior depth 140 of the right craniocaudal mammogram view 120, and the reporting application 65 may use this information to store information about the annotation 150, including a location (for example, right breast) and depth (posterior depth) of the marked lesion, which, as described below, may be used to automatically populate one or more fields of an electronic structured report.

Returning to FIG. 3, in response to receiving an annotation (at block 75) (as a manually-placed annotation, an automatically-generated annotation, or a combination thereof), the reporting application 65 automatically identifies an anatomical location associated with the annotation within the medical image (at block 160). In some embodiments, the reporting application uses the previously-determined divisions or depth graphics 145 to identify the anatomical location. For example, the reporting application 65 may identify that the marked lesion is positioned within a specific depth. In particular, as illustrated in FIG. 5, the reporting application 65 may identify that the annotation 150 is positioned within the posterior depth 140 of the right craniocaudal mammogram view 120.

Figure 7:
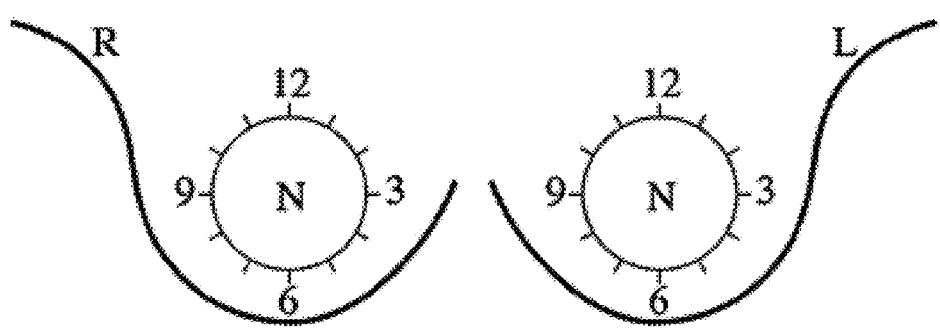
FIG. 7 illustrates a position represented using a clock standard from a frontal view.
Figure 8:
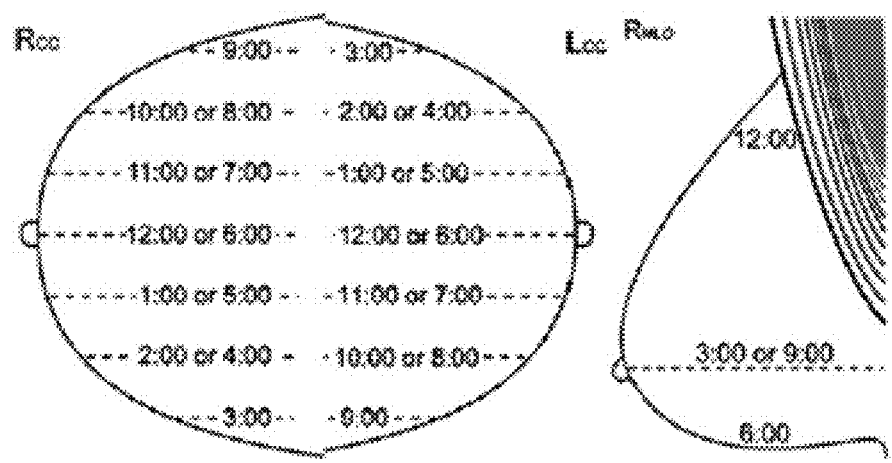
FIG. 8 illustrates a position represented using a clock standard from an oblique view and a craniocaudal.
Figure 9:
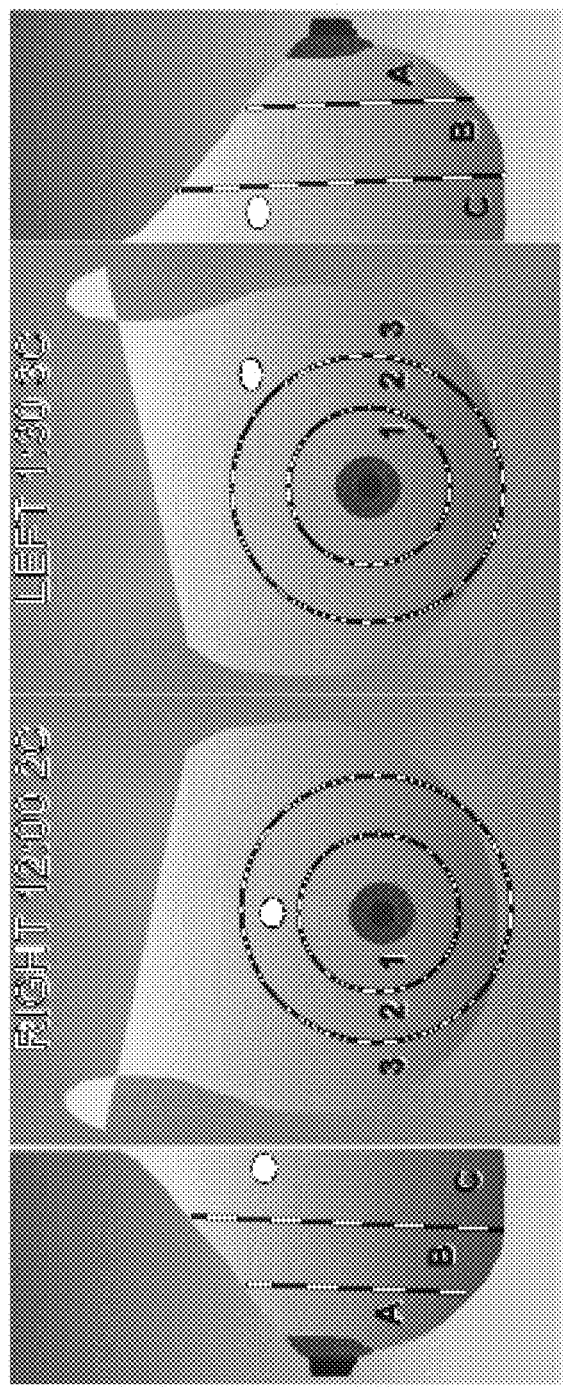
FIG. 9 illustrates a distance represented using standard zones from a frontal view.

In addition to or as an alternative to depth, the anatomical location associated with an annotation may include a position, which may be specified in various ways. For example, within a mammogram, a position may be represented as a clock position and a radial distance from a point of reference, such as an areola or a nipple. The clock position and the radial distance may use an available standard, which may evolve over time. For example, FIG. 7 illustrates a position represented using a clock standard from the frontal view. FIG. 8 illustrates the same position represented using a clock standard from the oblique view and the craniocaudal view. Similarly, FIG. 9 illustrates a distance from a point of interest in standard zones standard from the frontal view for describing a position. The particular standards used to specify a position of an annotation may be configurable through rules as described above for the labels and graphics.

The reporting application 65 may also use other types of image analytics to identify a particular anatomical structure or a particular position within an anatomical structure associated with an annotation. For example, the reporting application 65 may identify particular contours or shapes within a displayed medical image to identify a particular anatomical structure or position, which may be developed and refined using artificial intelligence and deep learning. Similarly, the reporting application 65 may use information associated with a displayed image, such as patient information, order information, and the like, to identify a particular anatomical structure or a particular location of an anatomical structure.

Returning to FIG. 3, in response to determining the anatomical location associated with the annotation using one or more of the techniques described above, the reporting application 65 automatically determines a location within an electronic structured report associated with the anatomical location based on a predetermined mapping (at block 260) and automatically populates the location of the electronic report based on the annotation (at block 270).

FIG. 10 illustrates a sample of a partially completed mammogram report 265. The report 265 includes one or more locations, such as a plurality of fields, including, for example, a procedure field, a comparison field, an indications field, and the like. One or more of the fields may be mapped to a particular anatomical structure (for example, a liver, a kidney), a particular anatomical location (for example, the left bilateral craniocaudal), or both. For example, a line item or section in a structured report may be associated with particular value type (for example, a finding, a type, and the like) and a particular anatomical location (for example, kidney, liver, left breast, and the like). These associations are stored in the predetermined mapping and may be manually-defined (received from an input mechanism or from a separate file), automatically generated using machine learning, or a combination thereof.

In some embodiments, the predetermined mapping similarly maps particular locations of a structured to other types of image characteristics or annotation characteristics. In other words, the mapping is not required to be based on anatomical locations of annotations and, hence, the structure report is not required to be anatomically-structured.

As one example, when the reading physician provides an annotation (for example, the annotation 150) marking a lesion, the reporting application 65 may automatically determine an anatomical location syntax for the lesion. The anatomical location syntax may have a format as follows: [Lesion #][finding type] [character] [laterality][depth][position on the clock][distance radial to a point of reference] [views seen]. In particular, when the reading physician provides an annotation on an image of the left breast, at a mid-breast depth, at a six o'clock position, at four centimeters (cm) radial to the nibble, seen on the craniocaudal and oblique view, the associated anatomical location syntax may read as follows: Lesion #1: [finding type] [character] left breast, mid-breast depth, six o'clock position, four cm radial to the nipple, seen on the craniocaudal and oblique views. The reporting application 65 may use the components of the anatomical location syntax to populate applicable locations of the structured report. In particular, the reporting application 65 may identify fields of a structured report associated with a left breast and mid-breast depth findings. In response to determining these fields, the reporting application 65 may populate these fields with the associated values included in the anatomical location syntax (for example, finding type, character, six o'clock position, four cm radial to the nipple, seen on the craniocaudal and oblique views, or a combination thereof).

As illustrated above, upon generating an anatomical location syntax, one or more of the components may not be completed. For example, when a reader marks a lesion on an image, the marking indicates a position of the lesion but may not necessary indicate other characteristics of the lesion, such as a finding (for example, malignant or benign). The reader may provide these details as part of generating the annotation. However, when the reader does not provide these details but these details would be mapped to particular data fields of the structured report (identified using the mapping described above), the reporting application 65 may highlight the fields that require completion by the reading physician, may prompt the reader for values, may automatically determine values for the fields, or perform a combination thereof.

The reporting application 65 may also automatically determine the location within a structured report based on the predetermined mapping and optionally, other annotations, rules, or a combination thereof. For example, the predetermined mapping or overriding rules (for example, specific to particular readers, workstations, and the like) may map particular values to locations of the structure report based on the existence or values of other annotations. For example, when a lesion is identified in a left breast, the predetermined mapping may place all information regarding the left breast in the structured report before the information regarding the right breast or vice versa.

Similarly, the predetermined mapping or overriding rules may specify the compiling and ordering of information for a structured report from multiple annotations. Accordingly, when the structure report is populated, the population may be based on other annotations. As noted above, the rules used to provide this type of customization may be associated with a reader, a workstation, an organization, an application, a patient, an imaging modality, an anatomical structure, the medical image, or a combination thereof. In some embodiments, the reporting application 65 may also preview compiled and ordered information for a reader and allow the reader to approve, reject, or modify the information.

For example, for a bilateral mammogram when there no suspicious findings in either breast, in both breasts, or just the left breast, one or more rules may specify that the information populated the structure report has a format as follows:
LEFT
SUSPICIOUS #1
SUSPICIOUS #2
BENIGN-APPEARING #1
RIGHT
SUSPICIOUS #1
SUSPICIOUS #2
BENIGN-APPEARING #1

However, when only the right breast has a suspicious finding, the rules may specify the following information order:
RIGHT
SUSPICIOUS #1
SUSPICIOUS #2
BENIGN-APPEARING #1
LEFT
BENIGN-APPEARING #1

Similarly, when either breast has no findings, the rules may specify the following information order that adds the text "NO SIGNIFICANT FINDINGS:"
RIGHT
SUSPICIOUS #1
SUSPICIOUS #2
BENIGN-APPEARING #1
LEFT
BENIGN-APPEARING #1

In some embodiments, the reporting application 65 (or other applications) may store and apply rules for mapping information into a report as well as supporting technology. For example, suppose there is a clinical report template that includes a FINDINGS section as follows:
FINDINGS:
LUNGS: Normal. No pneumonia.
PLEURA: Normal. No effusion.
MEDIASTINUM: Normal. No mass or adenopathy.
CARDIAC: Normal. No cardiac abnormality.
OTHER: Negative.

When doing an annotation when the annotation editing dialog is open, the reporting application 65 may use text-to-voice or text display to indicate to the reader the precise line item that is being edited. For example, the reporting application 65 may output audio data of "LUNGS" when a first annotation is created for any exam that is linked to this report template, since "LUNGS" is the first line item under findings. The reader may then interact with the reporting application 65, such as using an mouse, a microphone, and the like, to advance to another line item or return to a prior line item. Thus, without diverting attention to a separate report screen, the reader can control where annotation values (text) is entered into report. Furthermore, using deep learning methods, the reporting application may determine the anatomy being marked (such as within mediastinum) and advance to the appropriate line item in the report automatically. Again, rules can be used to perform this functionality that could be related to the reader, organization, modality, or exam type. In some embodiments, the rules may determine which of these embodiments is used for a particular instance (for example, whether text to voice is used, whether automated line item detection is used, or whether a manual action is needed to select the proper line item).

In some embodiments, the reader may provide values associated with an annotation (for example, finding, type, character, or combination thereof) by manually entering text, using speech recognition, or a combination thereof. Similarly, in some embodiments, these values may be automatically generated using as described above. Regardless of how the values are generated, the reporting application 65 may automatically transfer one or more of these values, such as labels, to the applicable fields of the associated structured report. These values may also be displayed or accessible through the annotation, such as by clicking on, hovering over, or otherwise selecting the annotation within the image.

In some embodiments, each time a reader generates a new annotation, adjusts an existing annotation, or provides a value for an annotation (for example, a finding), this activity may trigger the reporting application 65 to automatically transfer information to the structured report in the appropriate location or locations. For example, when a label is generated (and optionally approved by a reader), the reporting application 65 may automatically transfer the label to the structured report. It should be understood that the automatic transfer of information from image annotations to the structured report may be configured using one or more rules, stored data elements, or a combination thereof as described above for the automated labels and graphics. Also, as described above, in some embodiments, the reporting application 65 may be configured to automatically update a structured report based on modifications to existing annotations. Similarly, in some embodiments, a reader may manually modify a structured report. The reporting application 65 may, however, be configured to generate a warning in a situation where a manual update to the structured report is not compatible with an existing annotation.

In some embodiments, the reporting application 65 is also configured to display annotations mapped to structure report locations in a way to distinguish these annotations from annotations that are not mapped to structured report locations (depth guides and other visual guides). For example, when an annotation is mapped to a structured report, the reporting application 65 may update an annotation displayed within a medical image, such as by updating the color, size, font, animation, or graphic of the annotation, such that the annotation is displayed in a manner different from annotations not mapped to the structured report. In this manner, a reader may quickly and visually determine whether changes to an annotation will impact the corresponding structured report and identify where particular structured report information is being pulled from.

As previously noted, the reporting application 65 may use stored lexicon rules, position logic, or a combination thereof to reduce errors and aid a reader in reviewing images, such as multiple views of the same anatomical structure. In particular, when the reporting application 65 receives an annotation from a reader, the reporting application 65 may identify a stored rule based on the annotation. As described in more detail below, stored rules may specify constraints for an annotation, such as whether another related annotation is required and should be identified before the new annotation is committed or whether values for the annotation should be automatically-generated for manually-generated. As noted above, the rules may be based on particular readers, workstations, exam types, organizations, annotation type, anatomical structure, and the like. Accordingly, a stored rule may be identified based on the annotation or other characteristics related to the annotation, such as the reader making the annotation, the annotation type, and the like. After a stored rule is identified, the reporting application 65 executes the stored rule based on the annotation and automatically modifies the annotation accordingly or takes other automatic actions based on the execution. In some embodiments, the reporting application 65 provides one or more user interfaces that allow a user to specify or modify a rule. Alternatively or in addition, the reporting application 65 may be configured to automatically generate a rule, such as by using deep learning or other forms of machine learning and artificial intelligence.

For example, when the reading physician attempts to characterize a lesion as a "mass" but only labels the lesion on one view (one medical image), the reporting application 65 may initiate one or more automated actions, such as generating a warning, modifying the characterization, preventing the characterization, or a combination thereof, because the ACR BI-RADS® standard indicates that the term "mass" should only be applied to lesions visible on two views and these requirements may be implemented in one or more stored rules. In addition, upon marking a lesion in two views, the reporting application 65 may automatically update one or both of the annotations associated with the lesion to classify the lesion as a "mass" since the required markings in two views has been provided. Similarly, when the reader tries to characterize a non-anechoic ultrasound lesion as a "cyst," the reporting application 65 may initiate one or more automated actions. As another example, when the reader specifies a location of an annotation, such as a lesion associated with the annotation, that is not compatible with an automatically-determined location, the reporting application 65 may initiate one or more automatic actions. For example, when the reader describes a lesion as being in the eight o'clock position that the reporting application 65 assesses as being in the six o'clock position, the reporting application 65 may initiate one or more automatic actions.

Figure 11:
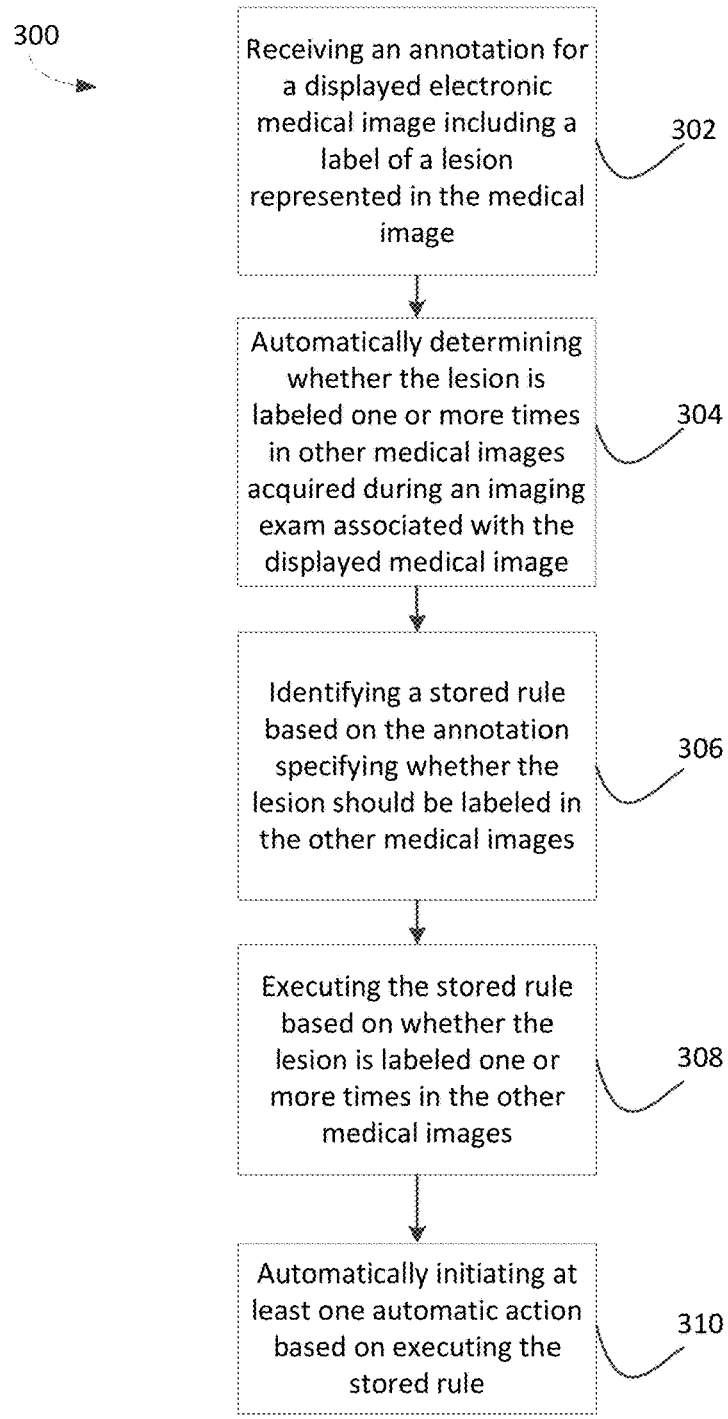
FIG. 11 is a flow chart illustrating a method of verifying an annotation using a stored rule performed using the system of FIG. 2.

For example, FIG. 11 illustrates a method 300 performed by the system 30 for reviewing medical images and, in particular, verifying an annotation using a stored rule. The method 300 is described below as being performed by the reporting application 65 (as executed by the electronic processor 40). However, the method 300 or portions thereof may be performed by one or more separate software applications (executed by the electronic processor 40 or one or more other electronic processors) that interact with the reporting application 65 (for example, as add-on functionality). As illustrated in FIG. 11, the method 300 includes receiving, with the reporting application 65, an annotation for a displayed electronic medical image (at block 302). The received annotation includes a label of a lesion represented within the medical image. In response to receiving the annotation, the reporting application 65 automatically determines whether the lesion is labeled one or more times in other medical images acquired during an imaging exam associated with the displayed electronic medical image (at block 304) and identifies a stored rule based on the annotation, wherein the stored rule specifying whether the lesion should be labeled in the other medical images (at block 306). For example, as described above, a stored rule may specify that when a lesion is labeled in a medical image, the lesion cannot be characterized as a "mass" unless the same lesion is also labeled at least one other view of the same anatomical structure (for a total of two labels). The stored rules may also be customized. For example, the stored rule may be associated with a reader, a workstation, an organization, an application, a patient, an image modality, an anatomical structure, the medical image, or a combination thereof. Accordingly, the reporting application 65 is configured to identify the stored rule based on the assigned reader, the workstation being used, an organization associated with the reader, and the like.

As illustrated in FIG. 11, in response to identifying the applicable stored rule, the reporting application 65 executes the stored rule based on whether the lesion is labeled one or more times in the other medical images (at block 308), and automatically initiates at least one automatic action based on executing the stored rule (at block 310). As described above, the at least one automatic action may include generating a warning (visual warning, audible warning, tactile warning, or a combination thereof), updating the annotation, deleting the annotation, and the like. For example, in some embodiments, the reporting application 65 automatically updates the annotation to characterize the lesion as a "mass" when the lesion is marked in the required number of views.

Figure 12:
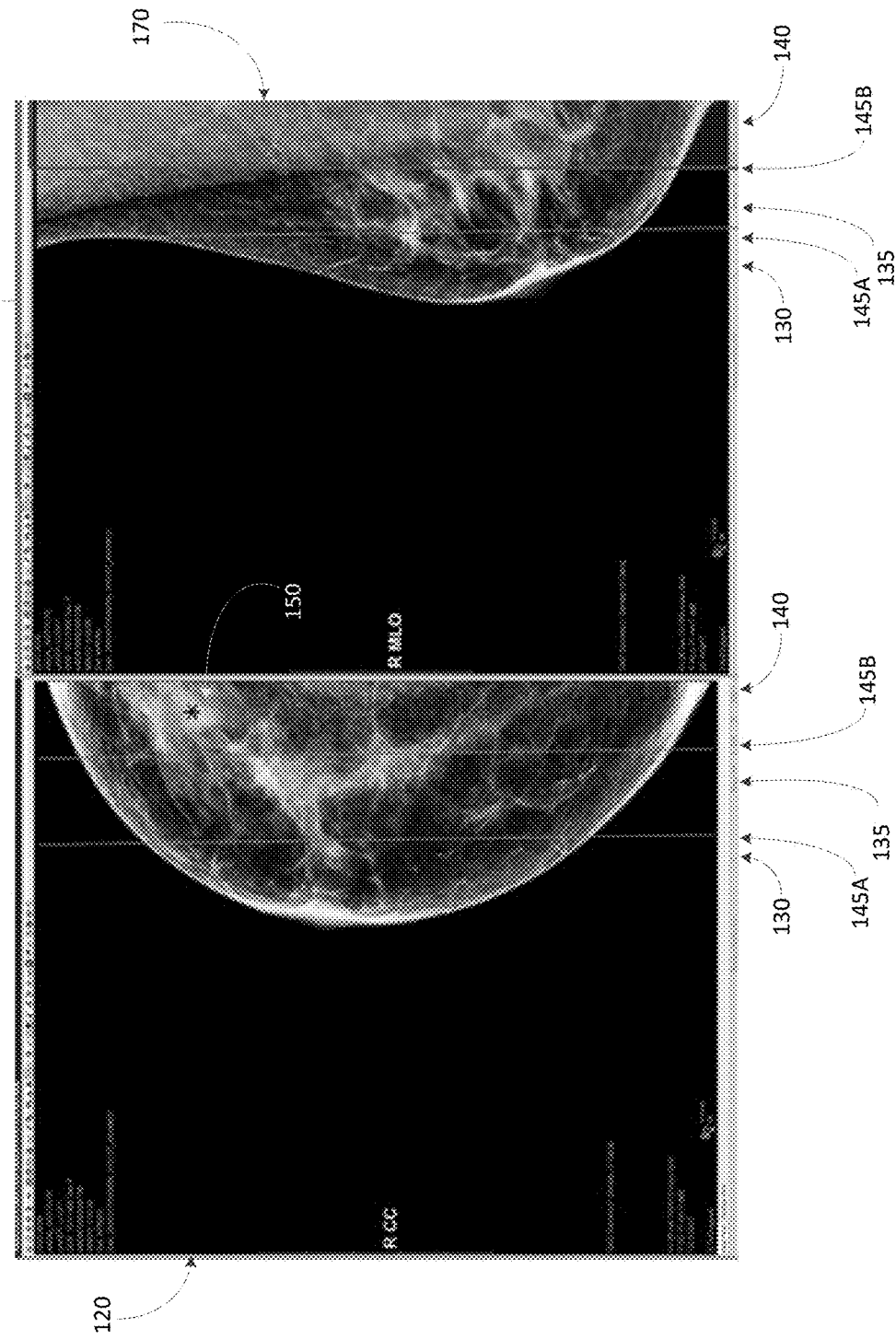
FIG. 12 illustrates a right craniocaudal mammogram view and a mediolateral oblique mammogram view with a matching location graphic.

In addition, in some embodiments, the reporting application 65 automatically generates a matching location graphic in response to receiving an annotation within a medical image. For example, as illustrated in FIG. 12, the annotation 150 represents a lesion. In response to the lesion being marked in one view (manually or automatically), the reporting application 65 automatically indicates one or more locations (each including, for example, a position, a depth, or both) at which the lesion should appear on another available view (in the same exam or different exams). In some embodiments, the reporting application 65 may generate multiple candidate locations for a lesion in one view based on the marking of the lesion in another view. In some embodiments, when multiple potential locations are marked, the reporting application 65 may score or rank the candidate locations (for example, by likelihood of location).

Figure 13:
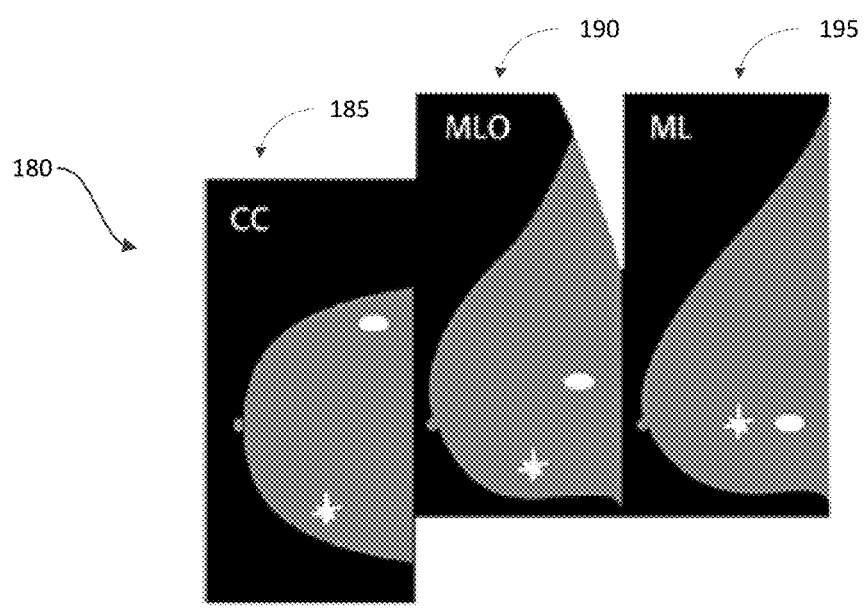
FIG. 13 schematically illustrates a diagram of a craniocaudal view, a mediolateral oblique view, and a mediolateral view of a right breast representing a triangulation process.

The matching location graphic 170 may mark a region or area within a medical image, such as within a rectangular frame. For example, as illustrated in FIG. 12, when the annotation 150 is positioned within the posterior depth 140 of the right craniocaudal mammogram view 120 and the reporting application 65 may automatically generate and display a matching location graphic 170 in the posterior depth 140 of the right mediolateral mammogram view 125. As illustrated in FIG. 12, the matching location graphic 170 may be represented as a highlight of the posterior depth 140 of the right mediolateral mammogram view 125. In some embodiments, at least a portion of the matching location graphic 170 is transparent. Similarly, as illustrated in FIG. 13, when a lesion is automatically or manually marked on a prior exam, the reporting application 65 may automatically mark one or more candidate locations for the lesion on the current exam or vice versa. Also, in some embodiments, the reporting application 65 determines and labels the obliquity of the matching location graphic 170.

In some embodiments, the reporting application 65 performs the location matching using triangulation. For example, FIG. 13 illustrates, from left to right, a diagram 180 of a craniocaudal mammogram view 185, a mediolateral oblique mammogram view 190, and a mediolateral mammogram view 195 of a right breast. These views may be used to perform triangulation, where a position of a lesion on any one of the three views may be inferred from the relative position of any two of the other views. For example, a lesion that is in the lateral breast may appear to be more superior on the mediolateral oblique mammogram view 190 than on the mediolateral mammogram view 195.

Figure 14:
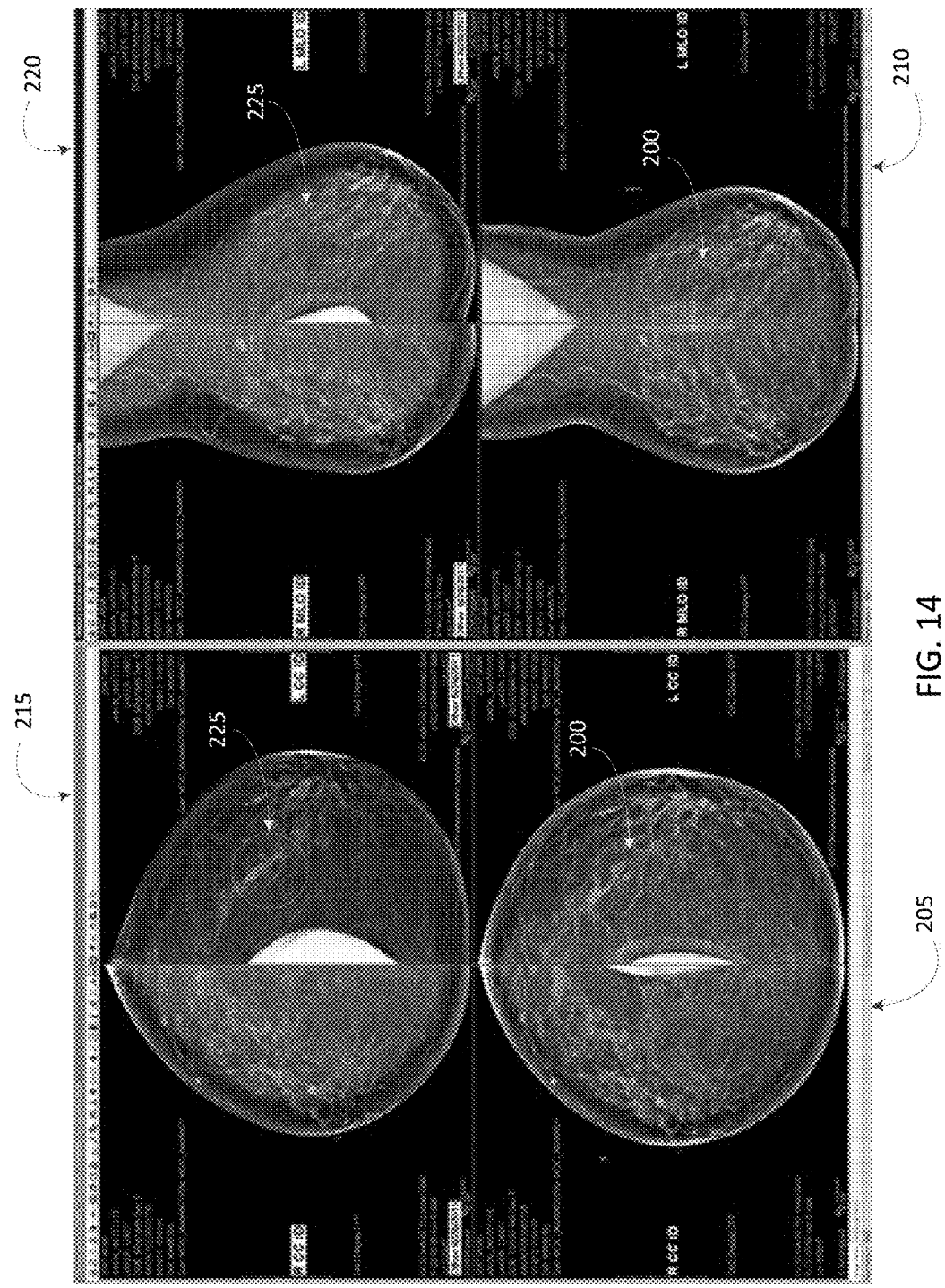
FIG. 14 illustrates location matching based on depth and position on a clock.

Alternatively or in addition, the reporting application 65 may perform location matching based on the radial distance from a point of reference, such as the areola. For example, as illustrated in FIG. 14, in the lower row of images, a circle 200 marks a small mass on a left craniocaudal mammogram view 205 and a left mediolateral mammogram view 210. The reporting application 65 may automatically indicate one or more candidate locations of the small mass in the relevant prior exams using, for example, the techniques described above. In particular, as illustrated in FIG. 14, the reporting application 65 may automatically indicate that the most likely prior location of the small mass in a prior left craniocaudal mammogram view 215 and a prior left mediolateral mammogram view 220 by a larger circle 225.

Figure 15:
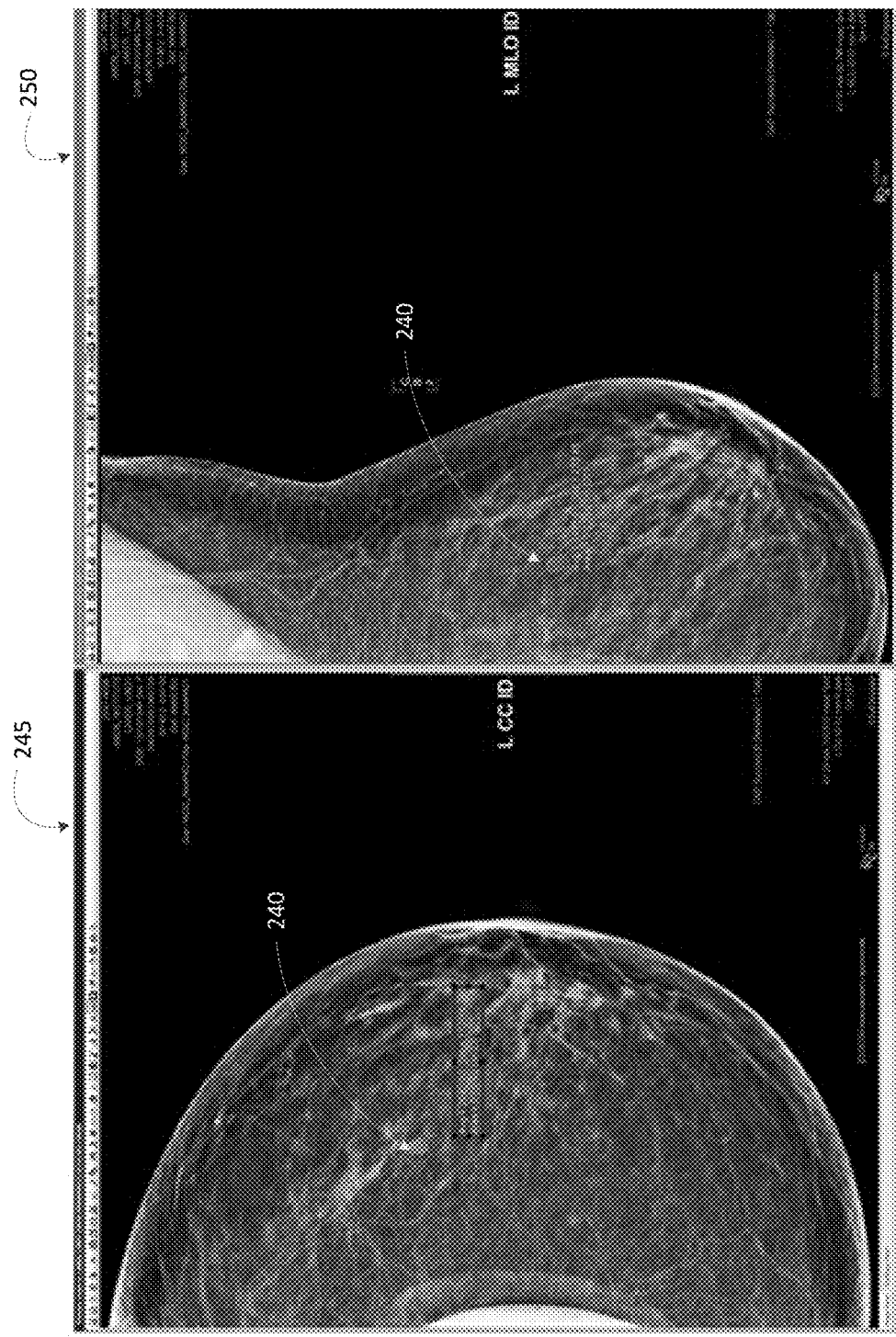
FIG. 15 illustrates lesion matching based on location and morphology.

In some embodiments, the reporting application 65 may perform location matching by performing lesion matching based on location, morphology, or a combination thereof. For example, as illustrated in FIG. 15, an annotation may mark a perimeter or border of a lesion 240 on the left craniocaudal mammogram view 245 and on the left mediolateral oblique mammogram view 250 of a left breast. The marking of the lesion 240 may be manually generated or automatically generated. When the marking of the lesion 240 is automatically generated, the marking of the lesion 240 may be the result of CAD or may be semi-automated where the reader marks the lesion 240 and the reporting application 65 detects the border of the lesion 240. The reporting application 65 may use the detected border to identify a similar border in another image that may represent the marked lesion in that image. In some embodiments, the reporting application 65 may also characterize the lesion 240 as a mass or calcifications. Further, the reporting application 65 may subcategorize masses, calcifications, or both. The reporting application 65 may use these characterizations to further identify matching lesions or potential matching locations.

As noted above, in some embodiments, when a lesion is marked in one view (manually or automatically) and the reader tries to mark the same lesion depicted in another view in a region or location that is not compatible with the initial marking of the lesion, the reporting application 65 may be configured to initiate one or more automatic actions, such as automatically generating a warning (for example, a visual warning, an audio warning, or a combination thereof). For example, when an index lesion is marked in the anterior depth 130 of the right craniocaudal mammogram view 120 and the reader tries to mark that same lesion in the posterior depth 140 of the right mediolateral mammogram view 125, the reporting application 65 may generate a warning.

Alternatively or in addition, when the reader tries to mark a lesion in a location that is not compatible with a marking of the same lesion on a particular view, the reporting application 65 may automatically mark the lesion as a second index lesion. Conversely, when a reader tries to mark a second index lesion in one view but a possible compatible lesion is present on another view, the reporting application 65 may automatically generate a warning, automatically mark the lesion as the same index lesion, or perform a combination thereof.

In addition, in some embodiments, the reporting application 65 also determines whether two annotations are compatible (for example, using configurable logic) based on geometry morphology (for example, in addition to the previously-described depth and location matching). For example, a lesion that is rod-shaped on one view likely cannot be circular on another view and also have a diameter larger than the rod.

Figure 16:
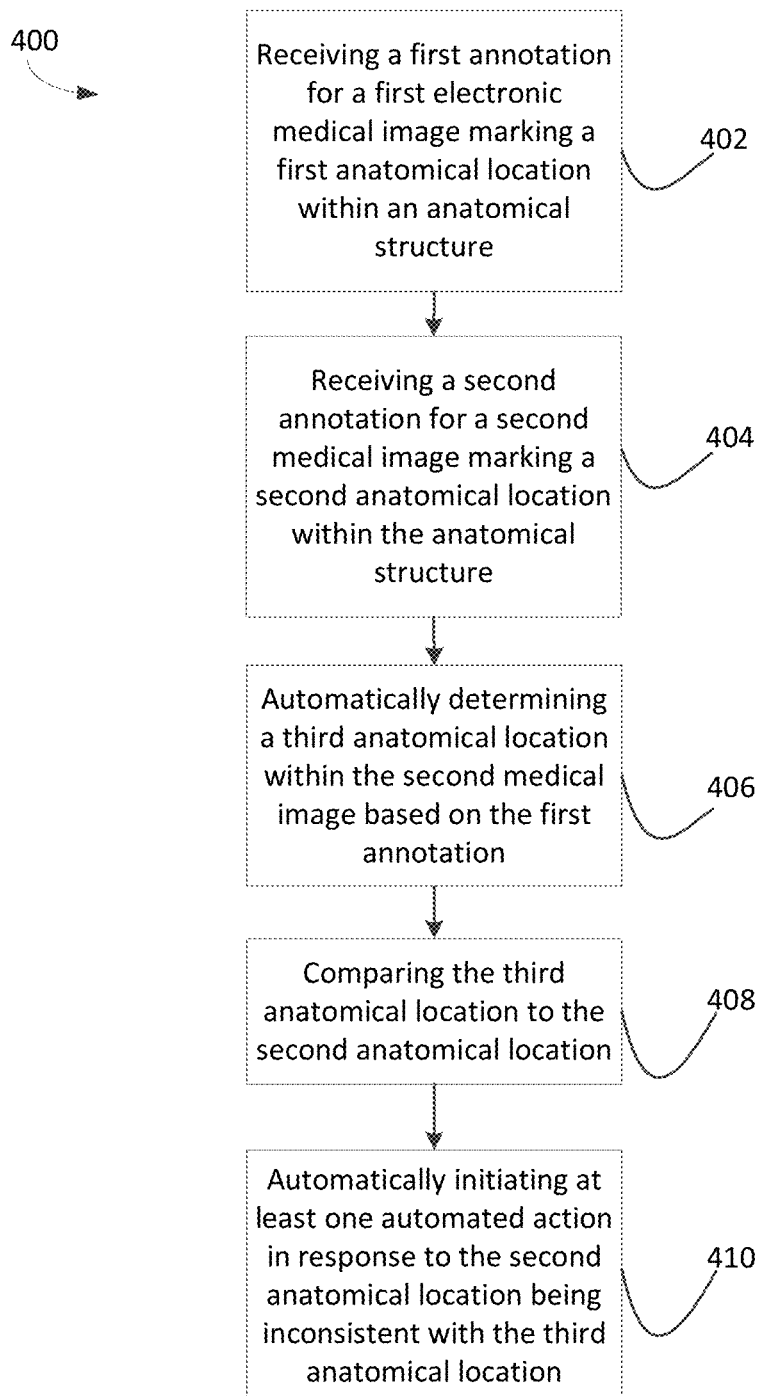
FIG. 16 is a flow chart illustrating a method of checking for consistent annotations performed using the system of FIG. 2.

For example, FIG. 16 illustrates a method 400 performed by the system 30 for reviewing medical images, and, in particular, checking for consistent annotations. The method 400 is described below as being performed by the reporting application 65 (as executed by the electronic processor 40). However, the method 400 or portions thereof may be performed by one or more separate software applications (executed by the electronic processor 40 or one or more other electronic processors) that interact with the reporting application 65 (for example, as add-on functionality).

As illustrated in FIG. 16, the method 400 includes receiving, with the reporting application 65, a first annotation for a first electronic medical image marking a first anatomical location, wherein the first medical image represents an anatomical structure from a first view (at block 402). The first annotation may be automatically-generated, such as by the reporting application 65, or may be manually-generated. The method 400 also includes receiving, with the reporting application 65, a second annotation for a second electronic medical image marking a second anatomical location, wherein the second medical image represents the anatomical structure from a second view (at block 404). Based on the first annotation, the reporting application 65 automatically determines a third anatomical location within the second medical image (at block 406) and compares the third anatomical location to the second anatomical location (at block 408). In other words, when two views are available for the same anatomical structure and one of the views includes an annotation, the reporting application 65 automatically determines where an associate annotation should be marked in the other view, such as where a lesion appears in one view based on being marked in a different view. As described above, the reporting application 65 may use a triangular process to determine the third anatomical location and may determine a depth, a position, or both for the third anatomical location.

In response to the second anatomical location being inconsistent with the third anatomical location, the reporting application 65 automatically initiates at least one automated action (at block 410). The at least one automated action may include automatically generating a warning, which may indicate a degree of match between the third anatomical location and the second anatomical location. Alternatively or in addition, the at least one automated action may include automatically updating the second annotation to include a label of a second lesion represented within the second medical image. The above verification process can be performed for images generated during the same imaging procedure or images generated during different imaging procedures. Also, in addition to comparing the anatomical locations, the reporting application 65 may also compare morphological of areas of the anatomical structure marked by the annotations.

The reporting application 65 may deploy the above described markings and warnings when a reader is manually marking lesions, when automated CAD is employed, or when a combination of manual and automated marking is employed. For example, CAD may identify multiple abnormalities on multiple views, and the anatomic localization functionality described above may aid a reader in understanding what marks on various views are likely depictions of the same lesions versus different lesions. Also, in some embodiments, the warning generated by the reporting application 65 may vary based on whether there is a clear mismatch, a borderline mismatch, or a match.

In some embodiments, the locating matching, annotation compatibility, and warnings are configurable as described above with respect to the labels and graphics. Also, it should be understood that although the matching location graphic 170 is described with reference to the craniocaudal mammogram view and the mediolateral mammogram view, the reporting application 65 may implement the matching location graphic 170 with any type of mammographic view. Furthermore, location and position matching may also apply to other types of medical images, such as chest radiographs, skeletal radiographs, and the like. Location matching may also apply to matching locations between the same or different views from exams obtained at different times. For example, when a lesion has been marked on a prior mammogram or was automatically computer-detected, the reporting application 65 may invoke location matching as described above to help the reader detect the lesion on a current exam.

In some embodiments, regardless of the imaging method used, the reporting application 65 is configured to automatically track lesions by index number, anatomical position, or both. For example, the reporting application 65 may be configured to automatically create a data structure, such as a table, tracking an index lesion on a series of prior exams and the current exam for one or more parameters, such as by tracking the size of the lesion. The data in the data structure may be weighed relative to existing reporting standards, such as Response Evaluation Criteria in Solid Tumors (RECIST) 1.1. Multiple index lesions may be tracked per patient, and a patient may have multiple serial exams.

For example, since lesions are localized by anatomical position, a table of serial results may be automatically created for each anatomically-specified lesion tracked over time. This tracking may apply to anatomical lesions, other anatomical findings, such as the progressive enlargement of an aneurysm, cardiac left ventricle, or intracranial aneurysm, or the progressive stenosis of a vessel or collapse of a vertebral body, or a combination thereof. Similarly, tracking may be used for implanted devices, such endotracheal tubes, chest tubes, Swan-Ganz catheters, peripherally inserted central catheter (PICC) lines, or other implants. When serial events are automatically or semi-automatically reported on a timeline, important clinical or historical events, such as when surgery or medical therapy was instituted and associated details, may also be superimposed on the table. For example, in some embodiments, the reporting application 65 triggers queries for reference data, treatment standards, clinical guidelines, reference image data, or a combination when a new annotation is generated (for example, when a new lesion is marked). The reporting application 65 may execute these queries based on configurable rules specific to the reader, the image type, the annotation, the patient, and the like. Also, when a lesion is marked on a current exam but was not marked on a prior exam, the reporting application 65 may be configured to attempt to mark the lesion in the prior exam (if it existed) and add data to the data structure for this prior exam. In other words, the reporting application 65 may be configured to add annotations to prior exams to create a comprehensive data structure for tracking lesions.

Figure 17:
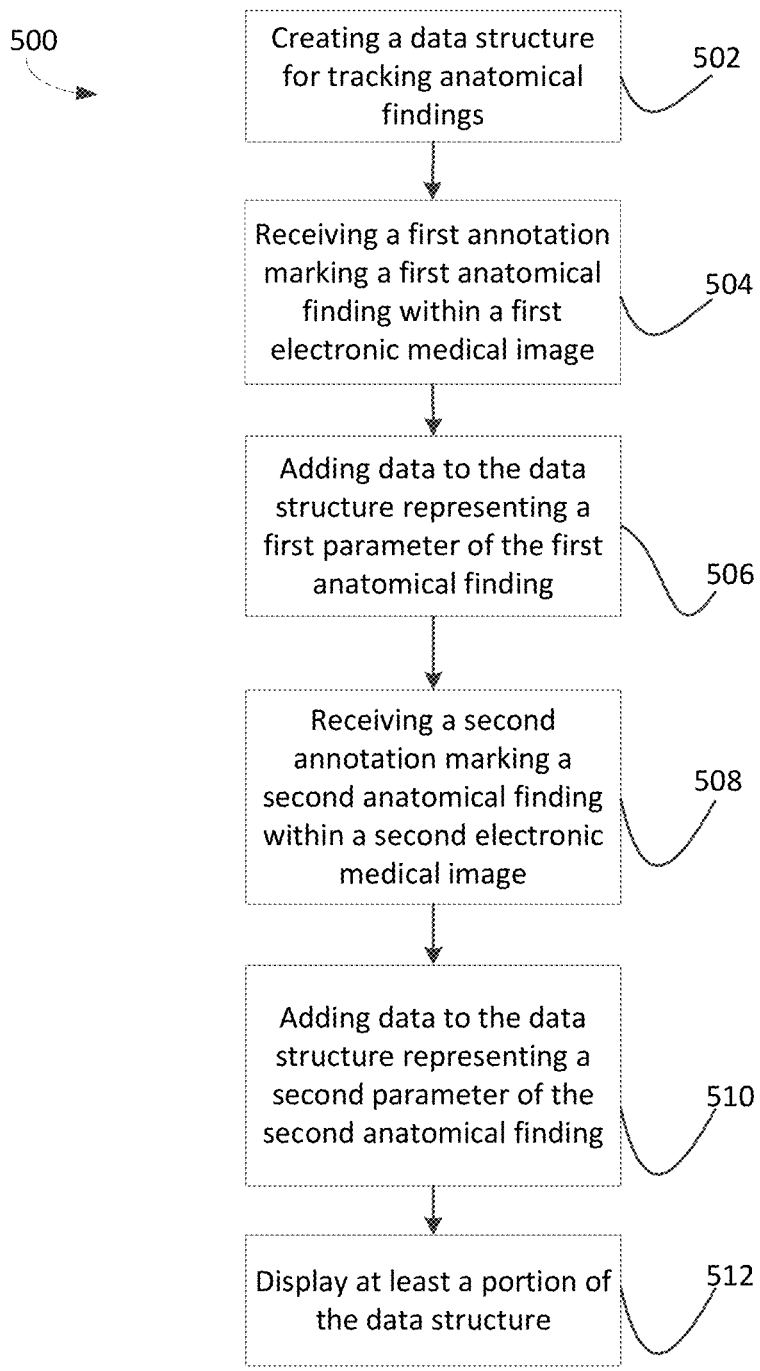
FIG. 17 is a flow chart illustrating a method of tracking lesions identified within one or more medical images performed using the system of FIG. 2.

For example, FIG. 17 illustrates a method 500 performed by the system 30 for reviewing medical images, and, in particular, tracking lesions identified within one or more medical images. The method 500 is described below as being performed by the reporting application 65 (as executed by the electronic processor 40). However, the method 500 or portions thereof may be performed by one or more separate software applications (executed by the electronic processor 40 or one or more other electronic processors) that interact with the reporting application 65 (for example, as add-on functionality).

As illustrated in FIG. 17, the method 500 includes creating, with the reporting application 65, a data structure, such as a table, for tracking anatomical findings (at block 502). The method 500 also includes receiving a first annotation marking a first anatomical finding within a first electronic medical image (at block 504) and adding data to the data structure representing a first parameter of the first anatomical finding (at block 506). The first parameter may be a size, a position, a type, or a combination thereof of the first anatomical finding.

The method 500 also includes receiving a second annotation marking a second anatomical finding within a second electronic medical image (at block 508) and adding data to the data structure representing a second parameter of the second anatomical finding (at block 510). Similar to the first parameter, the second parameter may be a size, a position, a type, or a combination thereof of the second anatomical finding. The first and second medical images may be included as an image study generating during the same imaging procedure or may be included in separate image studies generated during different imaging procedures. Also, in some embodiments, the first electronic medical image and the second electronic medical image may be the same image.

After adding the data to the data structure, the reporting application 65 displays at least a portion of the data structure (at block 512). The data tracked using the data structure may be displayed to a reader in various ways, including displaying the data structure or portions thereof, displaying statistics or trends based on the data structure, or a combination thereof. For example, in some embodiments, the reporting application 65 may analyze the data structure to identify a number of lesions marked in an image or an image study and this number may be displayed to a reader as a quick point of reference. Similarly, the reporting application 65 may analyze the data structure to identify whether any lesions have been marked in an image or an image study and provide an indication of this presence or lack thereof to the reader as a quick point of reference.

In some embodiments, the reporting application 65 is also configured to retrieve stored information associated with an annotation (for example, an anatomical location) and use the retrieved information to automate the reporting of follow-up exams, facilitate research or quality assessment activities, or perform a combination thereof. Furthermore, the stored information may be used to refine image analytics deep learning algorithms. Furthermore, the stored information may be stored in an interoperable format, such as a DICOM structured report, or a combination thereof. Accordingly, the anatomical location and related information for an annotation may be exported to an internal or external clinical report.

In some embodiments, embodiments of the invention may also inform readers of each patient's risk stratification so that readers may invoke a reading criterion shift based on clinical risk factors. As described below, the predictive value of a test may be influenced by the probability of disease within a studied population. Similarly, in addition to or as an alternative to manual criterion shifts based on pre-test probabilities of disease, computer image analytics may also perform better if a criterion shift is invoked based on a patient's clinical risk factors.

For example, assume a hypothetical imaging exam is 90% sensitive and 90% specific and is used to study a population where 99% of the patients are normal. Thus, although the exam has a 90% chance of detecting the one person with a true positive finding in this population, the exam will also produce then false positive findings. Accordingly, the positive predictive value of the exam is approximately 9% (for example, the number of true positives divided by the sum of the true positive and the false positives), the negative predictive value of the exam is 100% (for example, the number of true negatives divided by the sum of the true negatives and the false negatives), and the accuracy of the exam is approximately 91% (for example, the sum of the true positives and the true negatives divided by the sum of the true positives, the false positives, the true negatives, and the false negatives). Now assume the exam is used to study a population where 50% of the patients are normal. With this population, the exam will produce forty-five true positives, forty-five true negatives, five false positives, and five false negatives. Thus, the positive predictive value of the exam will be 90%, the negative predicative value of the exam will be 90%, and the accuracy of the exam will be 90%. Accordingly, by knowing clinical risk factors, an exam may be able to provide improved results.

As mentioned above, the review process involves the reading physician viewing the patient's clinical history (for example, the current exam 10 of the patient). Accordingly, in some embodiments, the reporting application 65 may be configured to compile pre-test clinical information (for example, the patient's relevant history and risk factors) and statistically analyze and report (display) the information to the reader. This allows the reader to concisely understand the pre-test probability of various disease states (for example, the probability of breast cancer). Pre-test probabilities of various likely concurrent, likely upcoming diseases, or both may also be automatically mapped into the clinical report based on defined rules, as described in more detail above. The reporting application 65 may also automatically highlight disease probabilities outside of a rules-specified range (with rules linked to factors such as a geographic location, a service organization, a reading physician preference, a referring physician preference, a patient characteristic, a genetic risk factor, another factor, or a combination thereof) to heighten the reader's attention. Also, in some embodiments, the probability of various disease states displayed to the reader may be dynamically updated as the reader generates or updates annotations for a displayed medical image. In particular, the identification of a particular anomaly or lack thereof in a displayed medical image may drastically impact the associated probability.

Figure 18:
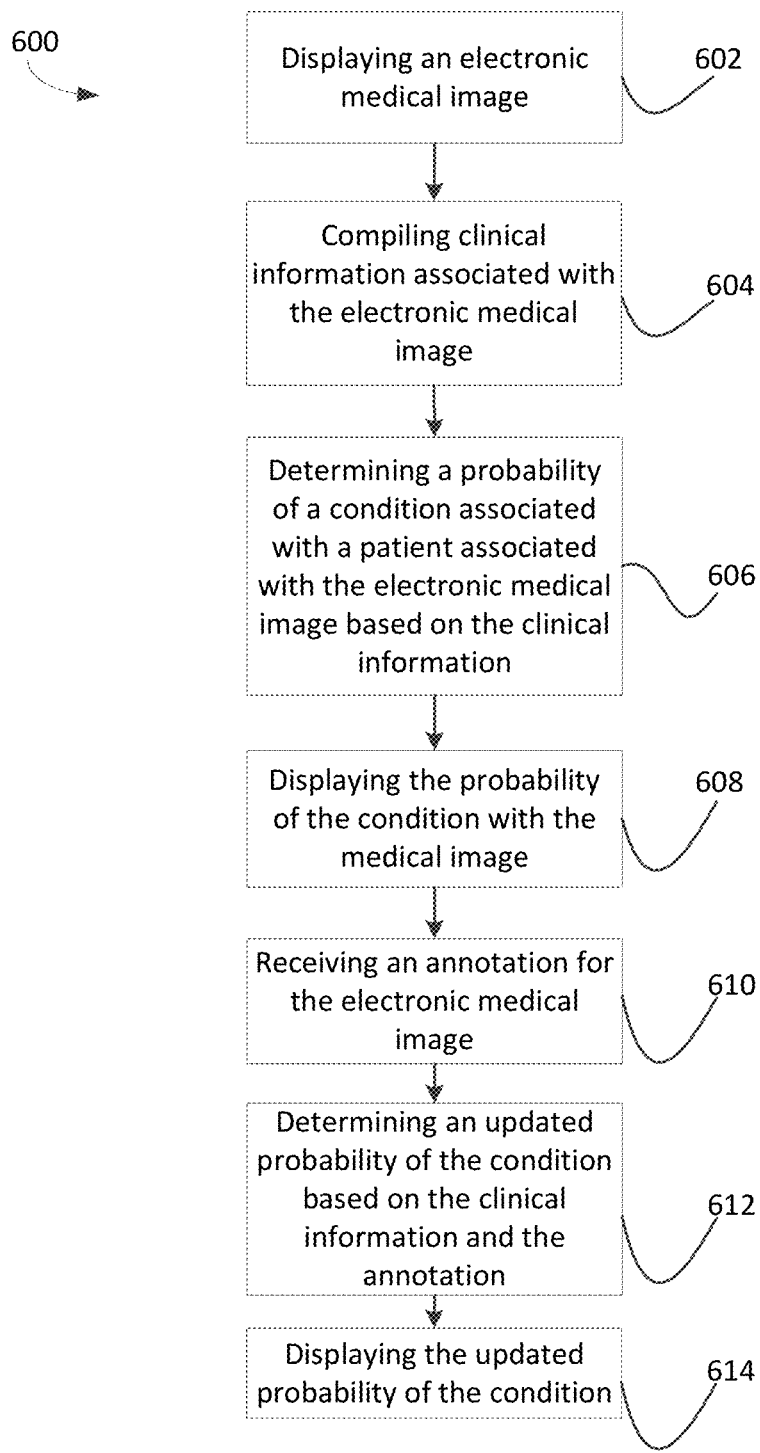
FIG. 18 is a flow chart illustrating a method of determining a probability of a condition associated with a displayed electronic medical image performed using the system of FIG. 2.

For example, FIG. 18 illustrates a method 600 for reviewing medical images, and, in particular, determining a probability of a condition associated with a displayed medical image. The method 600 is described below as being performed by the reporting application 65 (as executed by the electronic processor 40). However, the method 600 or portions thereof may be performed by one or more separate software applications (executed by the electronic processor 40 or one or more other electronic processors) that interact with the reporting application 65 (for example, as add-on functionality).

As illustrated in FIG. 18, the method 600 includes displaying an electronic medical image (at block 602). The method 600 also includes compiling clinical information associated with the electronic medical image (at block 604) and determining a probability of a condition associated with a patient associated with the electronic medical image based on the clinical information (at block 606). The clinical information may include patient history, a risk factor, a geographic location, a referring physician, a patient characteristic, or a combination thereof. The determined probability of the condition may be displayed with the medical image (in the same screen or on an associated parallel or overlapping screen) (at block 608). For example, in some embodiments, the probability of the condition may be displayed within a pop-up window or other associated window or screen. In other embodiments, the probability of the condition may be superimposed on the displayed medical image. Also, a plurality of probabilities may be displayed for the same or different conditions. In addition, the clinical information or a portion thereof may be displayed with the probability of the condition or available if a reader selects (clicks on, hovers over, and the like) the displayed probability.

As illustrated in FIG. 18, the method 600 also includes receiving, with the reporting application 65, an annotation for the electronic medical image (at block 610). The received annotation may be automatically-generated or manually-generated. In response to receiving the annotation, the reporting application 65 determines an updated probability of the condition based on the clinical information and the annotation (at block 612) and displays the updated probability of the condition (at block 614). The reporting application 65 may display the updated probability of the condition in place of or in addition to the original probability of the condition and, in some embodiments, may display the updated probability in a different manner than the original probability or may modify the original probability to indicate that the probability has been updated, such as by displaying the probability with a colored highlight, a flashing signal, or an audible tone. In some embodiments, the reporting application 65 also applies one or more stored rules. As noted above, the stored rules may be associated with a geographic location, an organization, a reader, a referring physician, a patient, or a combination thereof. The reader may use the updated probability to determine a finding for the medical image. Alternatively or in addition, the reporting application 65 may automatically generate a finding for the medical image based on the updated probability of the condition. For example, when the probability (original or updated) reaches a predetermined threshold, an automatic finding may be generated.

In some embodiments, when a number of exams of different patients require reading, the reporting application 65 may also order, group, or both a sequence of exams based on, for example, risk of abnormality. Alternatively or in addition, the reporting application 65 may order, group, or both a sequence of the exams based on other factors, such as type of abnormality, ordering location, patient sub-type, patient characteristics, automated computed analysis of the images plus clinical information, and the like. The reporting application 65 may also order exams using rules linked to an imaging location, a reader, a patient characteristic, another risk factor, or a combination thereof. The rules may also determine the routing, assignment or both of exams to specific reading physicians.

In addition to displaying probabilities, automatically ordering an exam sequence, or a combination thereof, embodiments of the invention may display other visual cues that help the reader understand at a glance that the patient has a higher or lower risk. For example, a colored highlight, a flashing signal, a tone, and the like may signal the reader as to the relative patient risk. The reading physician may then use the pre-test probability to shift the criteria for diagnosis so that the positive and negative predictive values are optimized. In some embodiments, instructions may be provided to the physician relating to how much to shift criteria, automatically provide or recommend a shift of the reader's reported results by an automatically adjusted factor based on pre-test calculated risk, or a combination thereof. For example, when a physician reports a finding as mildly suspicious in a patient that the reporting application 65 knows is high risk, the reporting application 65 may warn the reader that the patient is a high risk patient. Therefore, the reading physician may consider increasing the level of suspicion. Alternatively, the physician may indicate that a lesion is suspicious or of borderline suspicion. In response the proper description or BI-RADS® code, based on a combination of the physician's input and the patient's calculated risk, may be assigned. The preferences of the reading physician may be used as configuration guidelines in this situation.

In addition, the pre-test probability of various normal or abnormal conditions may be used to shift the criteria for computer-generated image analytics. For example, a threshold for diagnosing cancer may be adjusted based on the patient's risk in addition to the computer-detected morphology of a finding. Thus, the predictive value of the reported result may be optimized.

In some embodiments, the visual cues, audio cues, or both described above may appear on the same screen as the medical images so that the reader does not need to move his or her eyes from the medical images while reading. In some embodiments, the cues may appear transiently. The display of the cues may also be configurable using rules as described above for labels and depth graphics.

In addition, clinical information may appear on the images so that the reading physician may maintain his or her gaze on the images while reading. For example, the clinical information may include a label that shows where a patient has symptoms, where an intervention (for example, a biopsy, a lumpectomy, or a radiation therapy) was previously performed, or a combination thereof. In some embodiments, the key clinical information may appear transiently. Also, the key clinical information may be configurable by rules, as described above.

In some embodiments, the reporting application 65 may also be configured to automatically warn a reader regarding known personal biases, general reader biases, or a combination thereof. For example, a reader's probability of creating an abnormal report may be biased by the report he or she created on the previous patient or recent patients. For example, when reading a series of screening mammograms on different patients, a physician who has called the first patient back for additional workup may be more or less likely to call the next patient back for additional workup. In other words, even though each patient's evaluation should be considered independently, human factors may result in one reading affecting the results of subsequent readings. Accordingly, when such trends become apparent (for example, as a result of computerized analytics), a particular reader may receive automated prompts to protect against such biases. In addition, biases may be detected based on one or more patient characteristics. For example, a particular reader may have a track record of diagnosing cancer at an abnormally low frequency when presented with patients of a young age, an abnormally high frequency when presented with patients referred by a particular doctor or from a particular clinic, or a combination thereof. Accordingly, automated real-time analytics may prompt the reader to help protect against such biases.

Annotations may also be customized using one or more rules. For example, a reader may define one or more rules that indicate that when the reader adds an annotation with a particular shape (for example, a circle, an arrow, or the like) to a displayed medical image, that shape indicates a particular type of annotation, such as an annotation marking a lesion, an annotation marking a measure, and the like. Accordingly, in these situations, the reporting application 65 is configured to automatically populate one or more values associated with the annotation (for example, a description, a measurement, and the like), prompt the reader for one or more values associated with the annotation, or a combination thereof.

Figure 19:
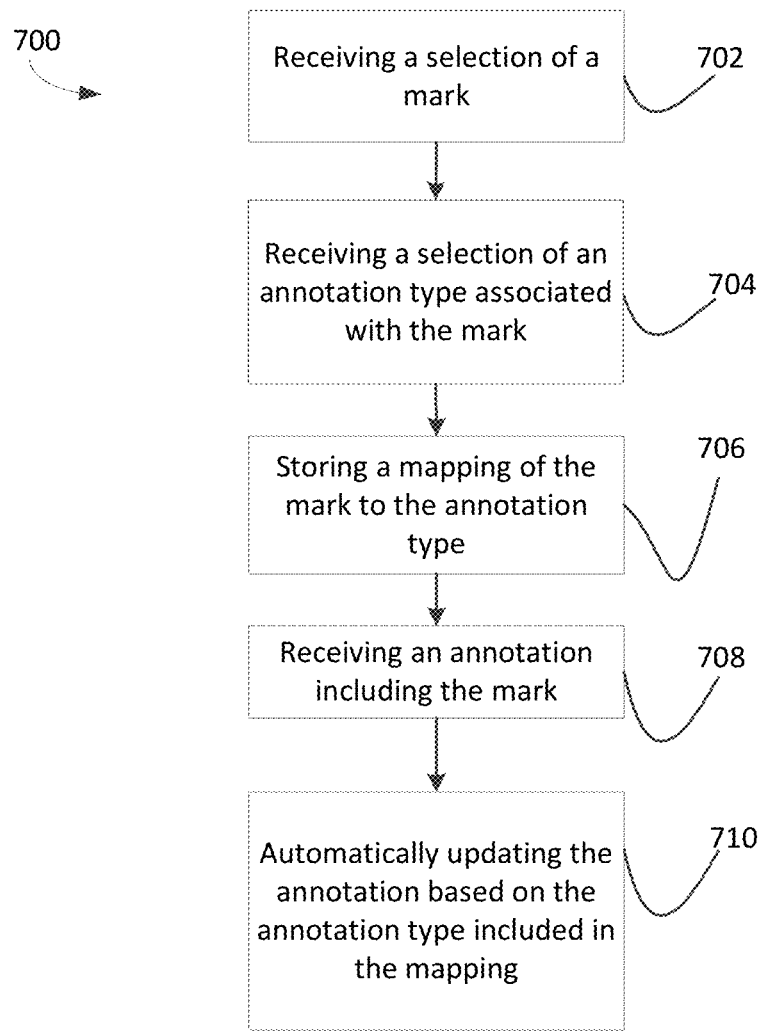
FIG. 19 is a flow chart illustrating a method of customizing annotations performed using the system of FIG. 2.

For example, FIG. 19 illustrates a method 700 performed by the system 30 for reviewing medical images, and, in particular, customizing annotations. The method 700 is described below as being performed by the reporting application 65 (as executed by the electronic processor 40). However, the method 700 or portions thereof may be performed by one or more separate software applications (executed by the electronic processor 40 or one or more other electronic processors) that interact with the reporting application 65 (for example, as add-on functionality).

As illustrated in FIG. 19, the method 700 includes receiving with the reporting application 65, through an input mechanism (a keyboard, a mouse, a touchscreen, and the like), a selection of a mark (for example, a particular shape, size, icon, and the like) (at block 702) and receiving, through the input mechanism (the same or a different input mechanism) a selection of an annotation type associated with the mark (for example, lesion type, benign region type, mass type, and the like) (at block 704). In some embodiments, the reporting application 65 display drop-down menus or other lists of predefined shapes, types, or a combination thereof for selection by a user. In other embodiments, a user may add an annotation to an displayed image, define the annotation as a particular type of annotation, and select a selection mechanism (a button, checkbox, radio button, hot key, and the like) to indicate to the reporting application 65 that other annotations identical (or substantially similar) to the annotation should be automatically defined as the same type.

In response to the received selections, the reporting application 65 stores a mapping of the mark to the annotation type (at block 706). The mapping may be associated with a particular reader, workstation, and the like and applied in a current reading session and, optionally, future reading sessions. Thereafter, when the reporting application 65 receives an annotation for a displayed electronic medical image that includes the mark included in the mapping (identical or substantial identical mark) (at block 708), the reporting application 65 automatically updates, based on the mapping, the received annotation based on the annotation type included in the mapping (at block 710). In other words, the reporting application 65 compares a received annotation to the marks included in the mapping to identify whether the received annotation includes a mark that is associated with a type within the mapping. When a received annotation includes a mark associated with a type within the mapping, the reporting application 65 automatically updates the annotation based on the associated annotation type within the mapping.

Similarly, the reporting application 65 may use one or more rules to determine how an annotation is completed. For example, as described above, an annotation (or portions of values thereof) may be manually completed, such as through entering text, dictation, and the like, may be automatically completed, such as using artificial intelligence or machine learning, or a combination thereof. Thus, a rule may specify whether a particular type of annotation (or all annotations) or a portion thereof is completed automatically or manually. These rules may be set on a reader basis, a site bases (imaging site, reading site, or both), exam type basis, and the like. In some embodiments, the rules also specify what values may be added to an annotation. For example, a rule may specify particular categories of values that may be added to an annotation, such as location, lesion characteristics, measurements, diagnosis, and the like. Also, in some embodiments, a rule may specify default values for an annotation, such as default diagnoses. Accordingly, using these rules and the customized annotations described above, a reader can add annotations to a displayed electronic medical image efficiently reducing computer resources and manual errors or inconsistencies.

Figure 20:
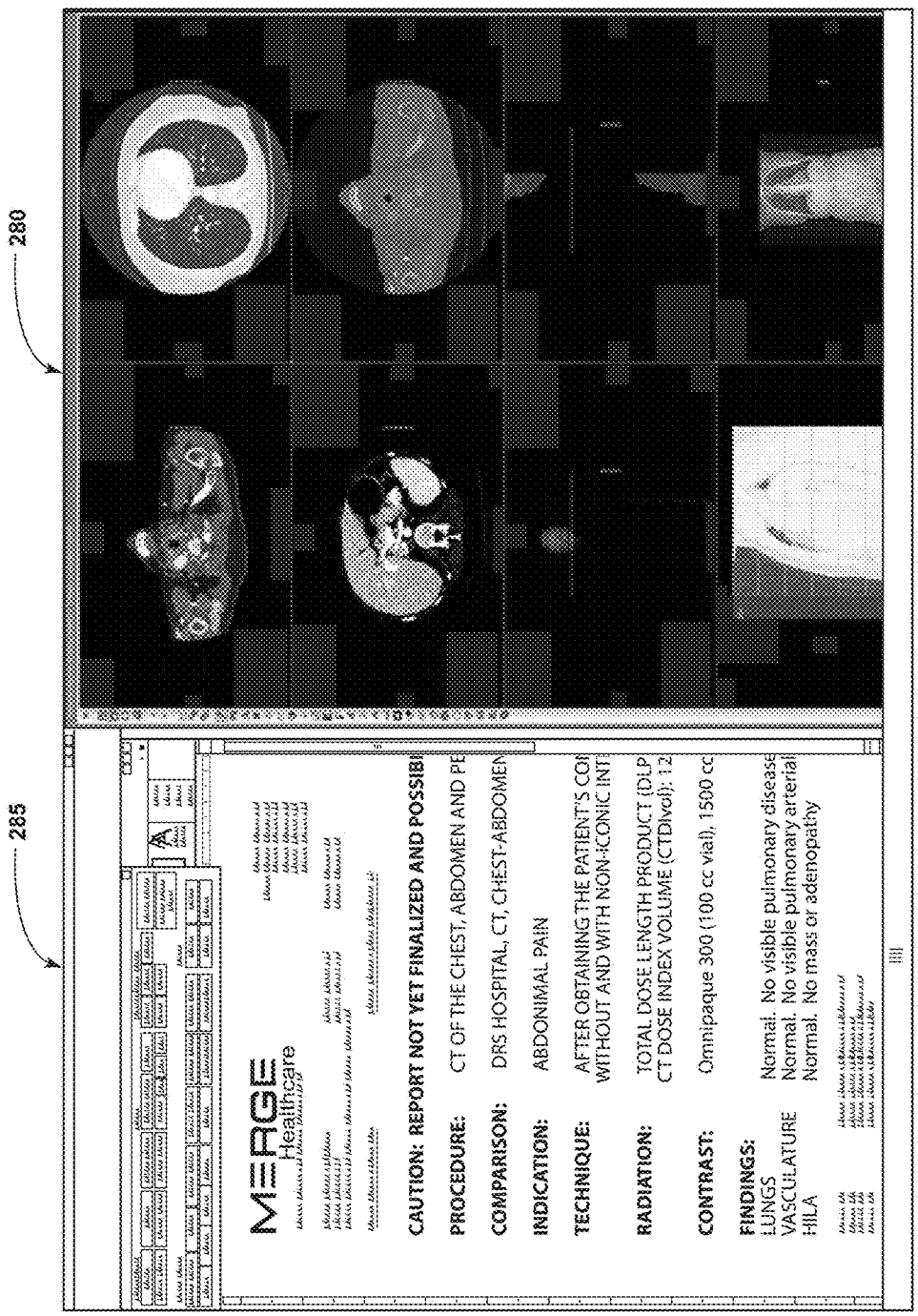
FIG. 20 illustrates a computed tomography exam and an associated report.
Figure 21:
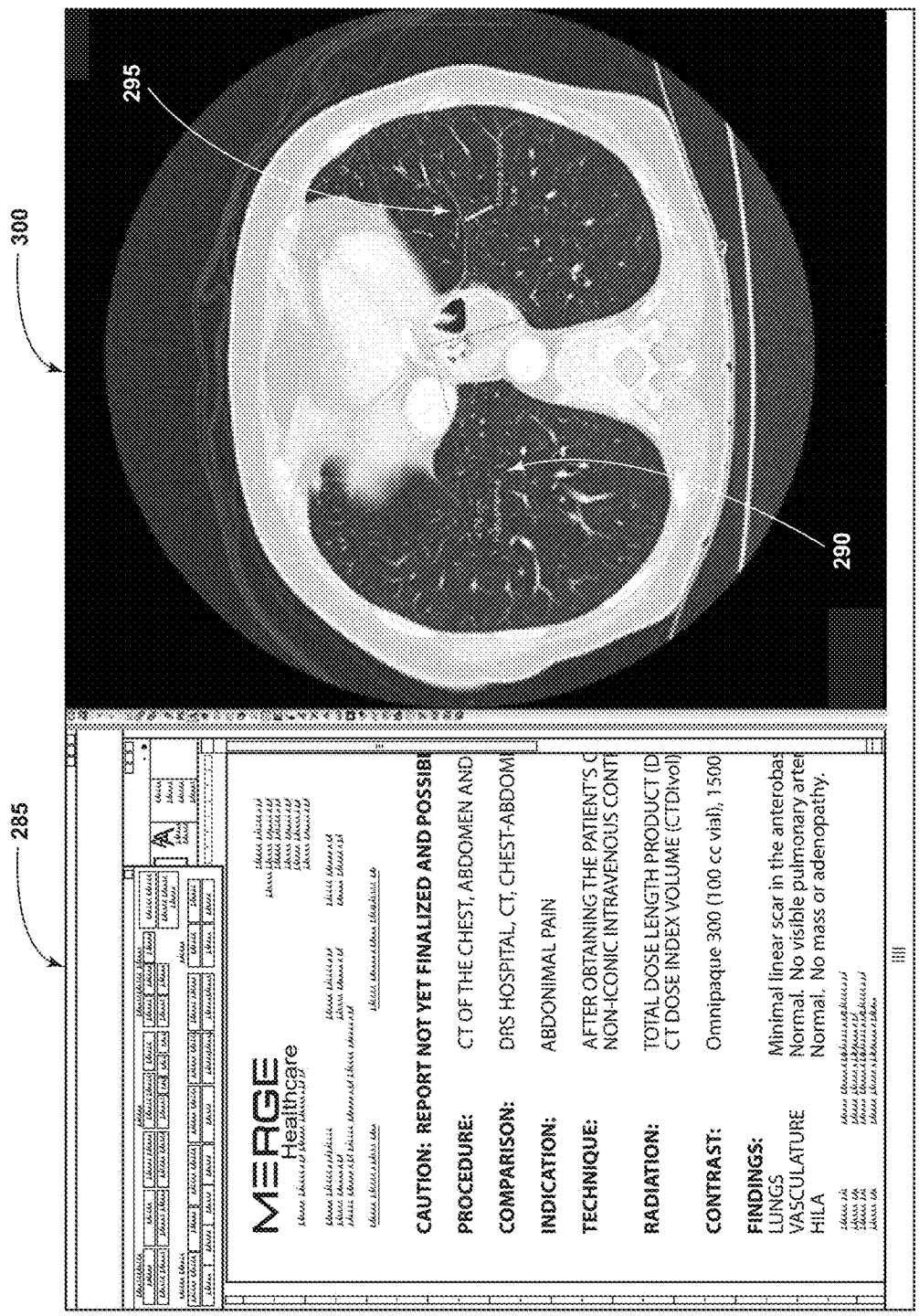
FIG. 21 illustrates a first finding label and a second finding label included on an image included in the computed tomography exam of FIG. 20.

As noted above, although the methods and systems described herein have been explained with references to mammography examples, the methods and systems described above may also be used with imaging exams other than mammography exams. For example, FIGS. 20 and 21 illustrate automated anatomical reporting of non-mammography exams. FIG. 20 illustrates a CT exam 280 and an associated report 285 according to some embodiments. FIG. 21 illustrates a first finding label 290 and a second finding label 295 on an image 292 included in the CT exam 280.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Also, the present invention may be a system, a method, a computer program product, or a combination thereof at any possible technical detail level of integration. The computer program product may include a computer readable storage medium (or media) having computer readable program instructions thereon for causing a processor to carry out aspects of the present invention.

The computer readable storage medium may be a tangible device that may retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (for example, light pulses passing through a fiber-optic cable), or electrical signals transmitted through a wire.

Computer readable program instructions described herein may be downloaded to respective computing/processing devices from a computer readable storage medium or to an external computer or external storage device via a network, for example, the Internet, a local area network, a wide area network, a wireless network, or a combination thereof. The network may comprise copper transmission cables, optical transmission fibers, wireless transmission, routers, firewalls, switches, gateway computers, edge servers, or a combination thereof. A network adapter card or network interface in each computing/processing device receives computer readable program instructions from the network and forwards the computer readable program instructions for storage in computer readable storage medium with the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or server. In the later scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described here in with reference to flowchart illustrations, the block diagrams of methods, apparatus (systems), and computer program products, or combinations thereof according to embodiments of the invention. It will be understood that each block of the flowchart illustrations, block diagrams, or both and combinations of blocks in the flowchart illustrations, block diagrams, or both, may be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart, block diagram block or blocks, or both. These computer readable program instructions may also be stored in a computer readable storage medium that may direct a computer, a programmable data processing apparatus, other devices, or a combination thereof to function in a particular manner, such that the computer readable storage medium having instructions stored therein comprises an article of manufacture including instructions which implement aspects of the function/act specified in the flowchart, block diagram block or blocks, or a combination thereof.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart, block diagram block or blocks, or a combination thereof.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams, flowchart illustration, and combinations of blocks in the block diagrams or flowchart illustration, may be implemented by special purpose hardware-based systems that perform the specified functions or acts or carry out combinations of special purpose hardware and computer instructions.

What is claimed is:

1. A method of generating an electronic structured report associated with a displayed electronic medical image, the method comprising:
   receiving an annotation for the displayed electronic medical image;
   automatically determining, with an electronic processor, an anatomical location within the displayed electronic medical image associated with the annotation;
   automatically determining, with the electronic processor, a location within the electronic structured report associated with the anatomical location based on a predetermined mapping; and
   automatically populating the determined location of the electronic structured report with data based on the annotation.

2. The method of claim 1, wherein receiving the annotation for the displayed electronic medical image includes receiving the annotation from a reader through an input mechanism.

3. The method of claim 1, wherein receiving the annotation for the displayed electronic medical image includes receiving an automatically-generated annotation.

4. The method of claim 1, wherein determining the location within the electronic structured report includes determining the location within an electronic, anatomically-structured report.

5. The method of claim 1, further comprising automatically dividing an anatomical structure represented in the displayed electronic medical image into a plurality of depths and displaying at least one depth graphic on the displayed electronic medical image based on the plurality of depths.

6. The method of claim 5, wherein displaying the at least one depth graphic includes displaying the at least one depth graphic transiently.

7. The method of claim 5, wherein displaying the at least one depth graphic includes displaying the at least one depth graphic in response to at least selected from a group consisting of receiving the annotation from a reader through an input mechanism and activation of a microphone.

8. The method of claim 5, wherein automatically determining the anatomical location associated within the displayed electronic medical image includes determining the anatomical location based on the plurality of depths.

9. The method of claim 5, wherein the at least one depth graphic includes an oblique line and further comprising automatically determining an angle of the oblique line based on information stored in a meta-file associated with the displayed electronic medical image.

10. The method of claim 1, further comprising automatically displaying a label at an anatomical position within the displayed electronic medical image.

11. The method of claim 10, wherein receiving the annotation for the displayed electronic medical image includes receiving a selection of the label.

12. The method of claim 10, wherein automatically displaying the label includes automatically displaying the label for at least one selected from a group consisting of an areola position, a subreolar position, a dermal position, a subdermal position, a subcutaneous position, an axillary position, and a chest wall position, an implant position.

13. The method of claim 10, wherein automatically displaying the label includes automatically displaying the label based on at least one rule associated with at least one selected from a group consisting of a reader, a workstation, an organization, an application, a patient, an imaging modality, an anatomical structure, and the displayed electronic medical image.

14. The method of claim 10, wherein automatically displaying the label includes displaying the label based on a position of a cursor within the displayed electronic medical image.

15. The method of claim 1, wherein receiving the annotation for the displayed electronic medical image includes receiving a label and a finding, wherein automatically determining the anatomical location within the displayed electronic medical image includes determining a position of the label within an anatomical structure represented in the displayed electronic medical image, wherein automatically determining the location of the electronic structured report includes determining at least one line item included in the electronic structured report associated with the position of the label and the anatomical structure, and wherein automatically populating the location of the electronic structured report based on the annotation includes populating the at least one line item with the finding.

16. The method of claim 1, wherein receiving the annotation for the displayed electronic medical image includes receiving a label and wherein automatically populating the location of the electronic structured report includes transferring the label to the location of the electronic structured report.

17. The method of claim 1, wherein automatically determining the anatomical location includes automatically generating an anatomical location syntax associated with the annotation and wherein automatically populating the location of the electronic structured report based on the annotation includes populating the location with at least one value included in the anatomical location syntax.

18. A system comprising:
an electronic processor configured to
  display an electronic medical image, receive an annotation for the electronic medical image,
  automatically determine an anatomical location within the electronic medical image associated with the annotation,
  automatically determine a location within an electronic structured report associated with the anatomical location based on a predetermined mapping;
  automatically populate the determined location of the electronic structured report with data based on the annotation; and
  automatically output data to a reader of the electronic medical image informing the reader of the location of the electronic structured report, wherein the output data includes at least one of visual data and audio data.

\* \* \* \* \*